(12) United States Patent
Johnson et al.

(10) Patent No.: US 9,710,599 B1
(45) Date of Patent: Jul. 18, 2017

(54) SYSTEM, METHOD AND COMPUTER PROGRAM PRODUCT FOR FACILITATING CLOUD-BASED RADIOLOGY DICOM RECEIPT, STORAGE AND MANAGEMENT

(71) Applicants: Joel G. Johnson, Winter Garden, FL (US); Steven T. Arcara, Orlando, FL (US); James Colin Jarrells, Winter Park, FL (US); Michael Douglas Muncy, Lexington, KY (US); Steven Joe Shearer, Winchester, KY (US); Richard Lee Carroll, Jr., Lexington, KY (US)

(72) Inventors: Joel G. Johnson, Winter Garden, FL (US); Steven T. Arcara, Orlando, FL (US); James Colin Jarrells, Winter Park, FL (US); Michael Douglas Muncy, Lexington, KY (US); Steven Joe Shearer, Winchester, KY (US); Richard Lee Carroll, Jr., Lexington, KY (US)

(*) Notice: Subject to any disclaimer, the term of this patent is extended or adjusted under 35 U.S.C. 154(b) by 400 days.

(21) Appl. No.: 14/046,906

(22) Filed: Oct. 4, 2013

Related U.S. Application Data

(60) Provisional application No. 61/709,566, filed on Oct. 4, 2012.

(51) Int. Cl.
*G06Q 50/22* (2012.01)
*G06Q 50/24* (2012.01)
*G06F 19/00* (2011.01)
*G06F 17/30* (2006.01)

(52) U.S. Cl.
CPC ...... *G06F 19/321* (2013.01); *G06F 17/30244* (2013.01); *G06F 19/328* (2013.01)

(58) Field of Classification Search
CPC .... G06F 19/321; G06F 19/327; G06F 19/345; G06F 19/3487; G06F 17/3028; G06F 19/3443; G06Q 50/22; G06Q 50/24; G06Q 10/10
See application file for complete search history.

(56) References Cited

U.S. PATENT DOCUMENTS

2013/0185331 A1* 7/2013 Conemac ............... 707/783

* cited by examiner

*Primary Examiner* — Maroun Kanaan
(74) *Attorney, Agent, or Firm* — Ashkan Najafi

(57) ABSTRACT

A cloud-based system, method and computer program product for obtaining and transferring diagnostic images to a secure data repository for archiving, accessing and future retrieval by patients, medical care providers and medical insurance providers. A variety of subsystems are provided for providing the aforementioned cloud-based radiology DICOM receipt, storage and management system wherein a web-based portal is communicatively coupled to a centralized repository thereby enabling a user to archive, retrieve and transfer diagnostic images between insurance companies and the medical community.

8 Claims, 49 Drawing Sheets

Figure 10

| Basic Information | Users | Locations | Modalities | Machines |
|---|---|---|---|---|

Name: Demo Test Provider 1
System Name:
NPI: 123456789
Payer ID: 123456
Tax ID: 123456789
Provider Number: 99999
IP Address:
Address 1: 123 Anywhere Street
Address 2: Suite 123
City: Orlando
State: FL
Zip: 11111
Phone: 8598598559

[Update]

Resolve QA Issue

| | |
|---|---|
| Study Instance UID: | 1.3.46.670589.11.0.1.1996082307380006 |
| Study Date: | 3/30/1995 |
| Patient: | Michael Muncy |
| QA Issue: | Poor Image Quality |
| Issue Notes: | Missing Thumbnail |
| Resolution: | Provider Agrees to Re-shoot Patient ▾ |
| Description: | *Maximum of 200 characters* |

Submit

Unresolved QA Issues

| DOS | Last Name | First Name | DOB | Modality | Anatomy | Issue | Last Modified | Modified by | Routine |
|---|---|---|---|---|---|---|---|---|---|
| 03/20/2355 | Murray | Michae | 10/23/1975 | MR | | Poor Image Quality | 03/21/2011 | Knowmedinfo@gmail.com | ✓ |

Tag Study

| Study Instance UID: | 1.2.392.200046.180.2.1.1.1165222642286.1208221335412 |
|---|---|
| Study Date: | 8/22/2012 |
| Patient: | Michael Muncy |
| QA Tag: | Poor Image Quality |
| Physician / Radiologist: | Provider: --Choose One-- <br> User: --Choose One-- |
| Reason / Description: | *Maximum of 200 characters* |

Dashboard > View Study

View Study

| Study Instance UID | 1.2.332.200046.109.2.1.11652226.4286.120822.1335.41.2 | Date of Birth | 10/23/1975 | Anatomy | FOOT |
|---|---|---|---|---|---|
| Study Date | 8/22/2012 | Referring Physician | JBF^Funk^Joseph | # of Images | 3 |
| Patient | Michael Muncy | Modality | CR | | |

- ✓ Required Fields
- ✓ Patient Match
- ✓ Assign
- ✓ Read/Dictate
- ✓ Transcribe
- ◆ Sign
- ◇ Claim Match Would you like to sign this study?

Name: _____

[Sign]

- Mark Start Read
- View Images
- Request Overread
- Addend Read
- Mark as Abnormal
- Mark as Complete
- Download Images
- Back to Dashboard

SYSTEM, METHOD AND COMPUTER PROGRAM PRODUCT FOR FACILITATING CLOUD-BASED RADIOLOGY DICOM RECEIPT, STORAGE AND MANAGEMENT

CROSS REFERENCE TO RELATED APPLICATIONS

This application claims the benefit of U.S. Provisional Application No. 61/709,566 filed Oct. 4, 2012, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE DISCLOSURE

Technical Field

Non-limiting exemplary embodiment(s) of the present disclosure relate to medical data information systems and, more particularly, to a cloud-based system, method and computer program product for obtaining and transferring diagnostic images to a secure data repository for archiving, accessing and future retrieval by patients, medical care providers and medical insurance providers.

Background
Duplication and Inappropriate Utilization of Diagnostic Imaging Services The Journal of the American Medical Association along with other industry medical experts have cited that up to 25% of imaging tests were ordered inappropriately or for defensive medicine purposes only. This results in an estimated cost of $30 billion dollars or more and continues to rise yearly. Physicians self-referring for diagnostic imaging constitutes up to a 54% increase in imaging tests performed in non-hospital facilities in which the referring physician has a financial interest. The American Journal of Radiology cited this in a study concerning physicians self-referring to their own facilities. The Center for Information Technology Leadership at Harvard University identified that over 20% of hospital radiology tests are duplicates which represents approximately $20 billion of wasted spending a year nationwide.

Claim Fraud and Abuse

The U.S. Federal Government through the division of the F.B.I.'s Strike Force has estimated that $178 billion dollars of claim fraud and abuse occurred in 2010. They expect this number to reach $239 billion in 2015. Radiology comprises 3% to 10% of this nationwide problem based on opinions of medical experts.

Technical Quality of Images Lack Quality Assurance Validation

Board Certified Radiologists have identified that over 20% of the studies performed in the U.S. lacked technical image quality sufficient to make an interpretation and diagnosis.

Inability to Easily Search and Identify the Modalities Performed by Diagnostic Providers Insurance companies and government sponsored programs do not have the ability to readily identify the specific modalities performed by diagnostic providers. Medical management and nurse case management departments often need to perform research and make calls to determine the availability of modalities and procedures performed by their participating providers.

Diagnostic Imaging is not Appropriately Applied to Potentially Preventable Conditions and Hospitalizations The Agency for Healthcare Research and Quality has identified that over $29.6 billion in national medical costs are associated with potentially avoidable hospitalizations.

Inability to Generate Comprehensive Data and Analytics for Imaging and Radiology Managed Care Organizations have difficulty in managing the costs and quality associated with imaging and radiology services. Insurance industry experts have identified that data and reports are not readily available for managing radiology and imaging services.

Diagnostic Imaging Clinical Appropriateness

Managed Care/Insurance organizations need the ability to identify the clinical appropriateness of authorizing radiology procedures by deploying evidence based medicine guidelines.

Channeling Imaging Studies to Contracted Teleradiology Groups

Managed Care/Insurance organizations need the ability to route imaging studies to participating teleradiology groups for their professional interpretation of the diagnostic file.

Diagnostic Facility Contract Rates

Managed Care/Insurance organizations will benefit by having the facility contract rates available in the provider profile database enabling them to route patients to providers with preferred contract rates.

Epidemiology Studies

A non-limiting exemplary embodiment of the present disclosure, performs epidemiology studies of medical conditions and diagnoses of various segments of the insured populations utilizing the system.

Conventional attempts to solve at least one of the aforementioned shortcomings are disclosed by PACS software. However, such software includes only an image storage and digital imaging and communications in medicine (DICOM) viewer. See, for example, www.seemyradiology.com.

BRIEF SUMMARY OF THE DISCLOSURE

The present disclosure meets the above-mentioned needs by providing at least one of a system, method, and computer program product for providing a cloud-based system, method and computer program product for obtaining and transferring diagnostic images to a secure data repository for archiving, accessing and future retrieval by patients, medical care providers and medical insurance providers.

Regarding the shortcoming of duplication and inappropriate utilization of diagnostic imaging services, in a non-limiting exemplary embodiment, a web based software application (computer program product) is provided that enables diagnostic providers to upload imaging studies to the central repository via the Internet. A secure web based portal gives authorized users access to view the images 24 hours a day, seven days a week. The medical community and insurance industry will share viewing access to the imaging studies available in the repository and enable the healthcare industry to build accountability into the process. The application is HIPPA compliant and SAS-70 compliant for security and confidentiality of patient information. The insurance company using this present disclosure will receive administrative access and have additional functionality built into their user status in order to give them additional flexibility in utilizing the system. The application will run parallel to the insurance company's software and not infringe upon its proprietary applications and operating system.

The benefit is it reduces the duplication of imaging tests by permitting medical providers to share the viewing of the studies via our web based application. A provider located in a medical office, hospital, outpatient facility. Surgery center or nursing home will have the ability to view the imaging tests. As long as they have Internet access, the authorized user can connect to the central repository and view the patient's images with the online imaging viewer. The reduction in duplicate studies will result in significant savings to the insurance and healthcare industries.

Regarding the shortcomings of claim fraud and abuse, in a non-limiting exemplary embodiment, a relational database is provided that cross-references the images in its repository with the CMS-1500 and UB-04 medical claim form generated by patient encounters. The insurance company or government sponsored program will have the ability to generate a report of any claims that cannot be validated with a matching study archived in the repository.

This benefit gives the insurance company or government sponsored program the ability to suspend the claim for further investigation or deny its payment. If a medical claim cannot be supported by an imaging study, the payer will have the ability to research any suspicious claims. The insurance and healthcare industry will incur significant savings by detecting and reducing claim fraud and abuse pertaining to radiology services.

Regarding the shortcoming wherein technical quality of images lack quality assurance validation, in a non-limiting exemplary embodiment, a protocol is provided in a web based application that gives the radiologist or referring physician the ability to flag a study that is considered to be of poor technical image quality. The insurance company receives notification of the inadequate study and will determine if the study needs to be repeated by the facility. Payment for the study can be suspended or rejected until the study is considered of sufficient technical quality to make an interpretation and diagnosis. The insurance company will also have the ability to view the image via the secure web based portal and have one of their own medical experts review and confirm the technical quality of the study.

This benefit gives the insurance company the ability to be informed of studies that are considered to be of poor technical quality. The facilities performing poor quality studies can be identified and evaluated for quality issues. Corrective steps can be taken to suspend or reject payment of the studies and also suspend or remove the facility from their provider network.

Regarding the shortcoming of not being able to easily search and identify the modalities performed by diagnostic providers, in a non-limiting exemplary embodiment, an internal searchable database is provided that can identify the specific modalities and procedures performed by each of their participating diagnostic facilities. The insurance company can efficiently route the patient to an approved facility that performs the authorized modality or procedure needed to diagnose the patient.

This benefit assists the insurance company with routing the patient expeditiously to a participating facility that performs the appropriate diagnostic services. Patient satisfaction and quality of care will improve as a result of this value added feature.

Regarding the shortcoming of diagnostic imaging not being appropriately applied to potentially preventable conditions and hospitalizations in a non-limiting exemplary embodiment, the radiologist is provided the ability to identify if the imaging test is abnormal based on his/her interpretation and findings. The referring physician and insurance company will be forwarded an email notification identifying that the patient need follow up care based on receiving an abnormal diagnostic test. This deploys a system of checks and balance between the referring physician and the insurance company to ensure the patient does not slip through the healthcare system without getting follow up treatment.

This benefit reduces potentially avoidable hospitalizations for conditions that could be treated in an outpatient setting. Expensive hospital admissions will be reduced by effectively coordinating medical care in a more cost effective outpatient environment. Accountability between the patient and referring physician for follow up treatment will become an integral part of the process.

Regarding the shortcoming of not being able to generate comprehensive data and analytics for imaging and radiology, in a non-limiting exemplary embodiment, a relational database captures extensive information on the patient, modality, procedure, diagnostic facility and imaging tests being performed by the insurance company's participating providers. Reports are generated for trending the utilization and developing effective cost containment strategies.

This benefit provides comprehensive data and analytics to support the medical management of imaging services and its appropriate utilization. The insurance company will be able to implement effective medical policies in order to reduce excessive expenses associated with imaging.

Regarding the diagnostic imaging Clinical Appropriateness, creating a relational database that will enable Managed Care organizations to search the (ACR) American College of Radiology's Clinical Appropriateness Criteria guidelines. By searching the database for clinical conditions, it will identify if the radiology procedure is clinically appropriate to perform the procedure based on evidence based medicine guidelines. The Managed Care organization will authorize or deny the procedure based on the ACR's current clinical protocol.

Genesis Vault will empower the Managed Care organization to make clinically appropriate medical authorization decisions based on industry standard clinical guidelines. This will reduce utilization of radiology procedures and improve quality for the patient by also reducing unnecessary exposure of radiation to the patient.

Regarding channeling imaging studies to contracted teleradiology groups, enables the Managed Care/Insurance organization the ability to channel the imaging studies for "professional" interpretation to Teleradiology groups that are contracted with them at preferred rates. Facilities will perform the "technical" component of completing the diagnostic study. It will then be routed for "professional" interpretation to the Teleradiology group in order to assemble a complete diagnostic file on the patient.

The Benefit: Genesis Vault enables the Managed Care/Insurance organization to save significant money on the "professional" interpretation of the diagnostic file. Typically the radiology groups will receive a percentage of billed charges for their services but with Genesis Vault enabling the studies to be routed to Teleradiology groups contracted at preferred rates, their medical expense will be significantly reduced.

Regarding diagnostic facility contract rates, provider profile built into its database for maintaining detailed information regarding the diagnostic facility. With the addition of the contract rate loaded into our provider profile, it enables the medical authorization department to channel patients to facilities with preferred rates. By having this information readily available in the provider profile, it expedites the search process and improves their efficiency.

The Benefit: Genesis Vault enables the Managed Care/Insurance organizations to direct patients to diagnostic facilities that are more cost effective in performing procedures. This will reduce their medical expenditures on diagnostic services by utilizing facilities with preferred rates.

Regarding epidemiology studies, capturing the diagnoses and medical conditions in our relational database. These are transferred to our data repository from the diagnostic facilities on the various studies performed. Tracking and trending of this medical information can be valuable in understanding the insured population's present and future medical conditions. Reports can be generated from the database for assembling information based on geography, gender, age, diagnosis, medical condition, etc.

The Benefit: Genesis Vault is an additional resource for compiling critical medical information on the insured population. Key information regarding medical conditions and diagnoses will be readily available to healthcare organizations utilizing our service.

Although, conventional software applications offer storage and DICOM image viewing. Our disclosure specifically deals with the payer and their interaction with the DICOM study and data instead of the provider only.

BRIEF DESCRIPTION OF THE SEVERAL VIEWS OF THE DRAWING

The novel features believed to be characteristic of this disclosure are set forth with particularity in the appended claims. The disclosure itself, however, both as to its organization and method of operation, together with further objects and advantages thereof, may best be understood by reference to the following description taken in connection with the accompanying drawings in which:

FIG. 3 provides a high level overview of the provider signup process as part of the onboarding program of the payer.

FIG. 4 provides a high level review of the basic user interface by which different users/roles access the information available to their user/role.

FIG. 5 provides a high level review of the payer user interface to demonstrate the major functions that are available to the payer/carrier in the system.

FIG. 6 provides a high level review of the provider user interface to demonstrate the major functions that are available to the provider in the system.

FIG. 7 provides a high level review of the major administrative functions that are available throughout the system.

Figure 10:
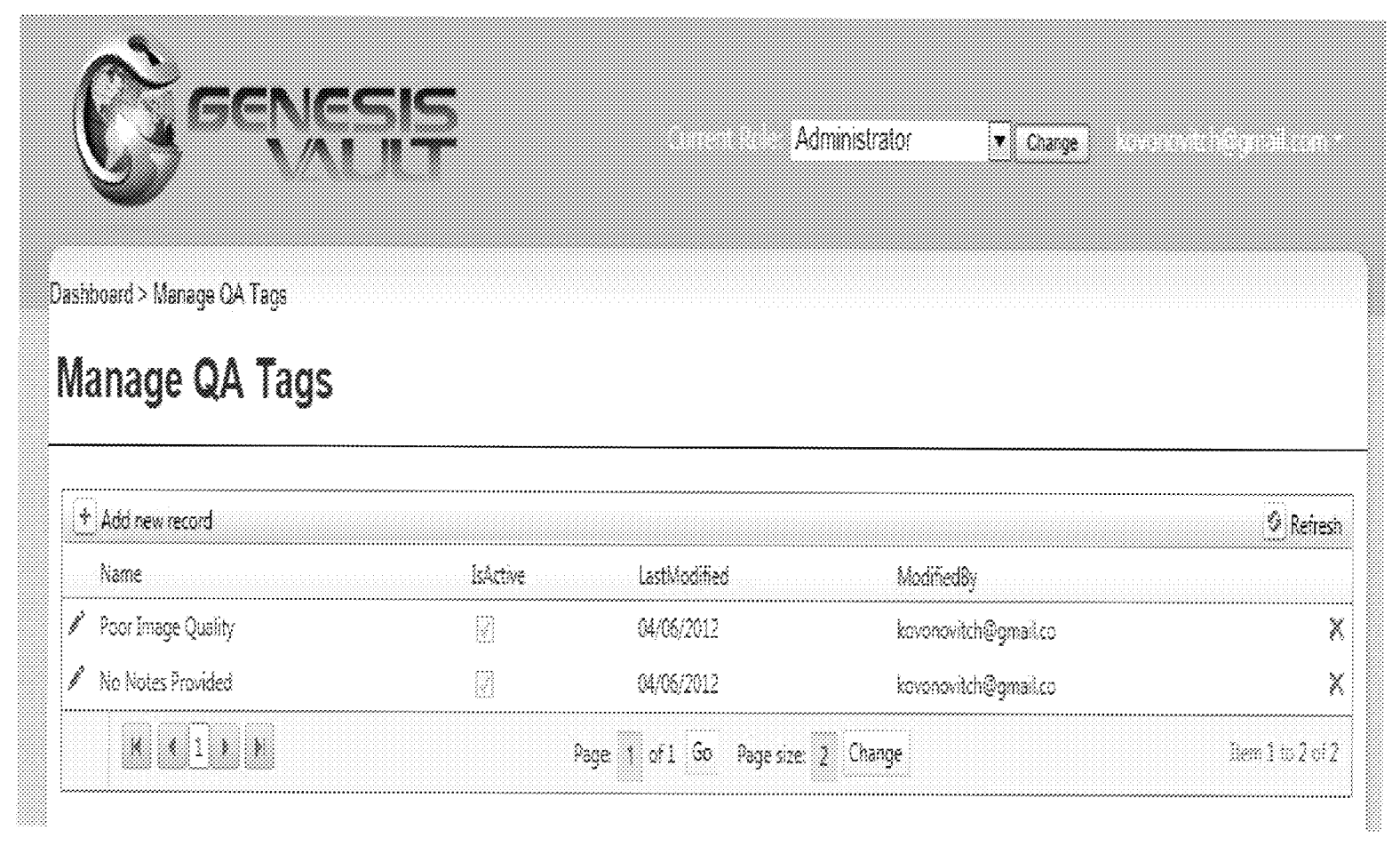

FIG. 10 is the Provider DICOM Image Viewer and QA Tagging Screen, which displays the Manage Providers to Carriers as well as the Manage QA Tags functionality. The Manage Providers to Carriers functionality allows administrators the ability to tie providers to one to many payers/carriers. The Manage QA functionality allows administrators the ability to add QA tags to the system that are then displayed to the providers.

FIGS. 11-12 are exemplary screen shots illustrating the carrier dashboard;

Figure 13:
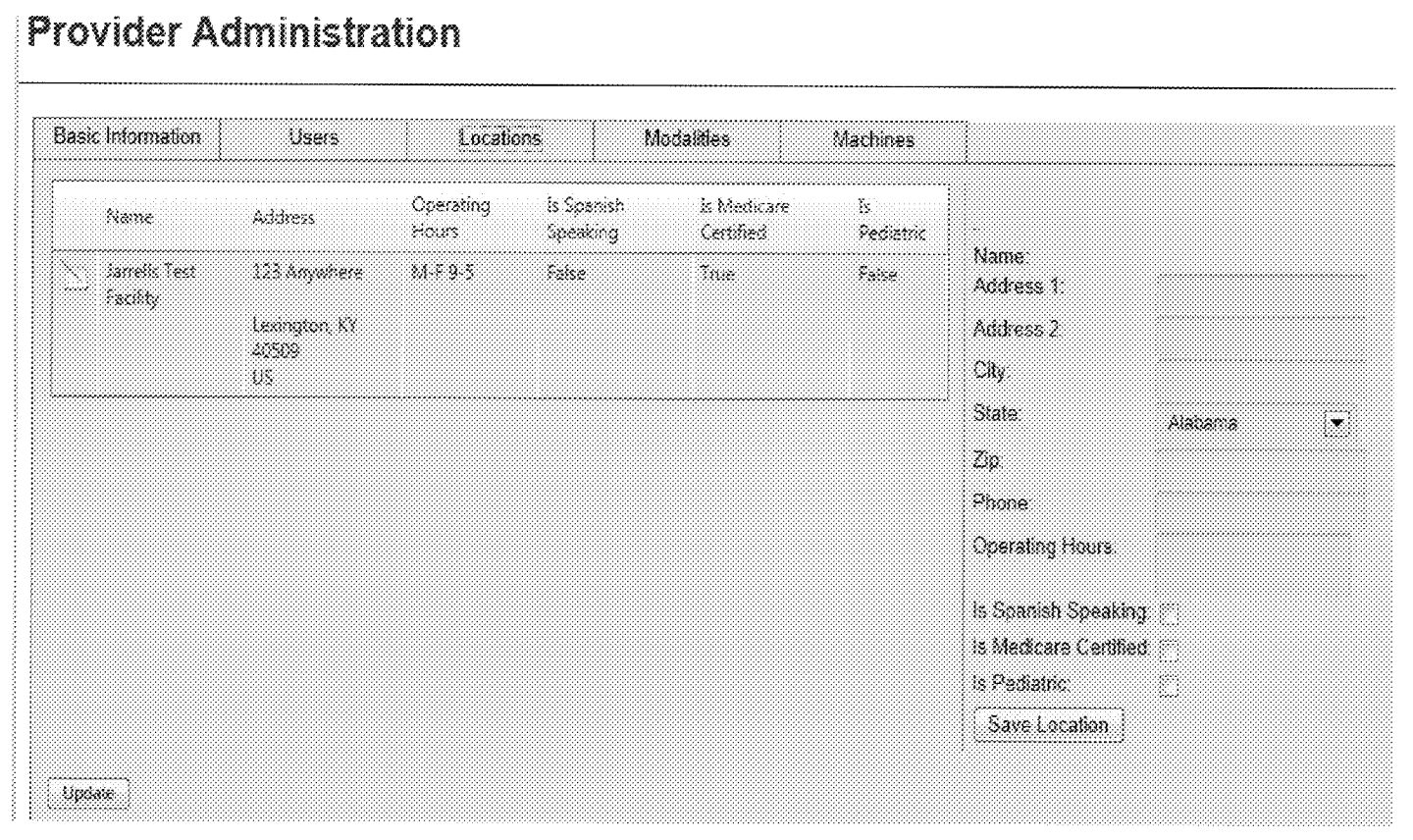
Figure 14:
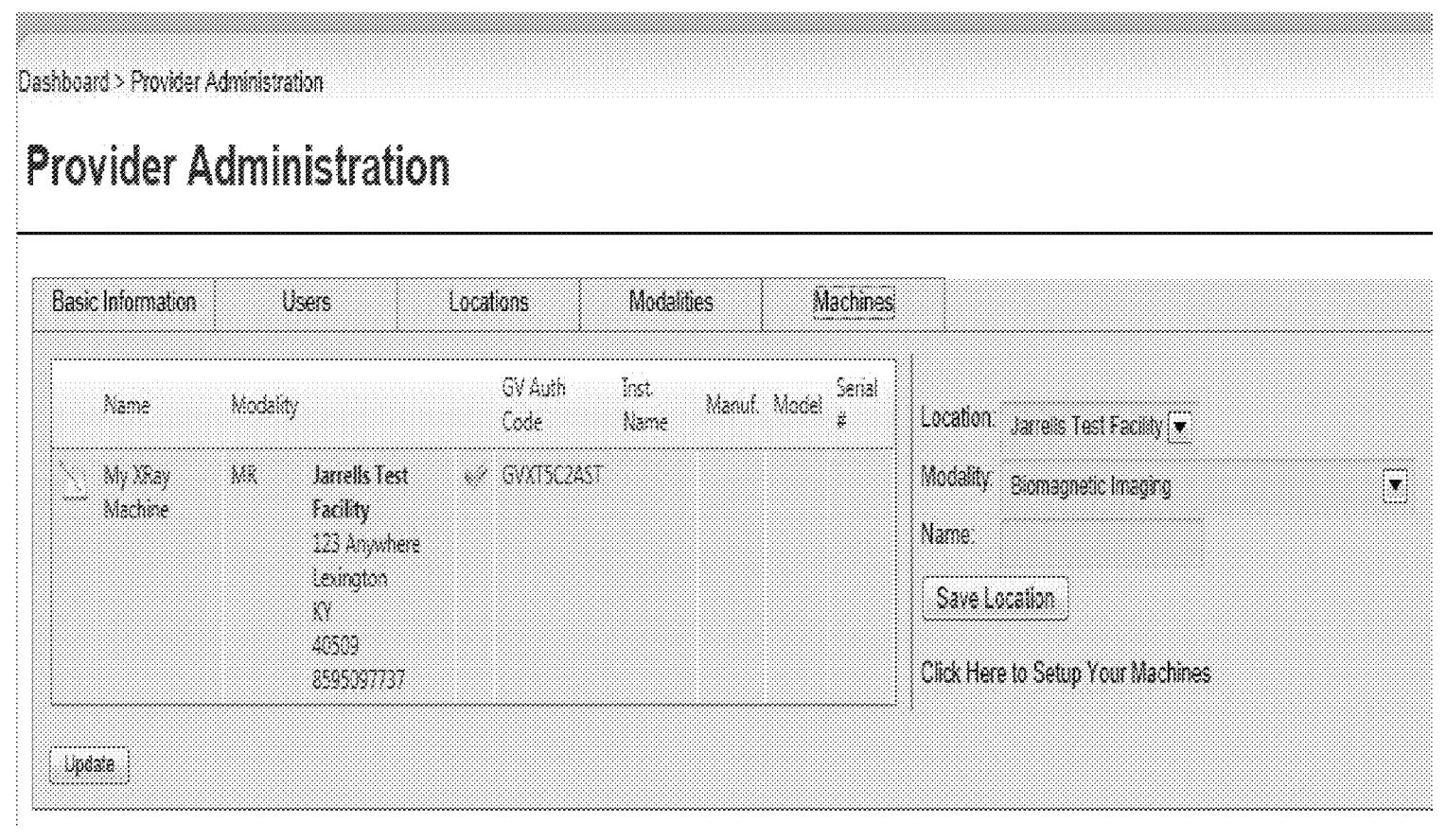
Figure 16:
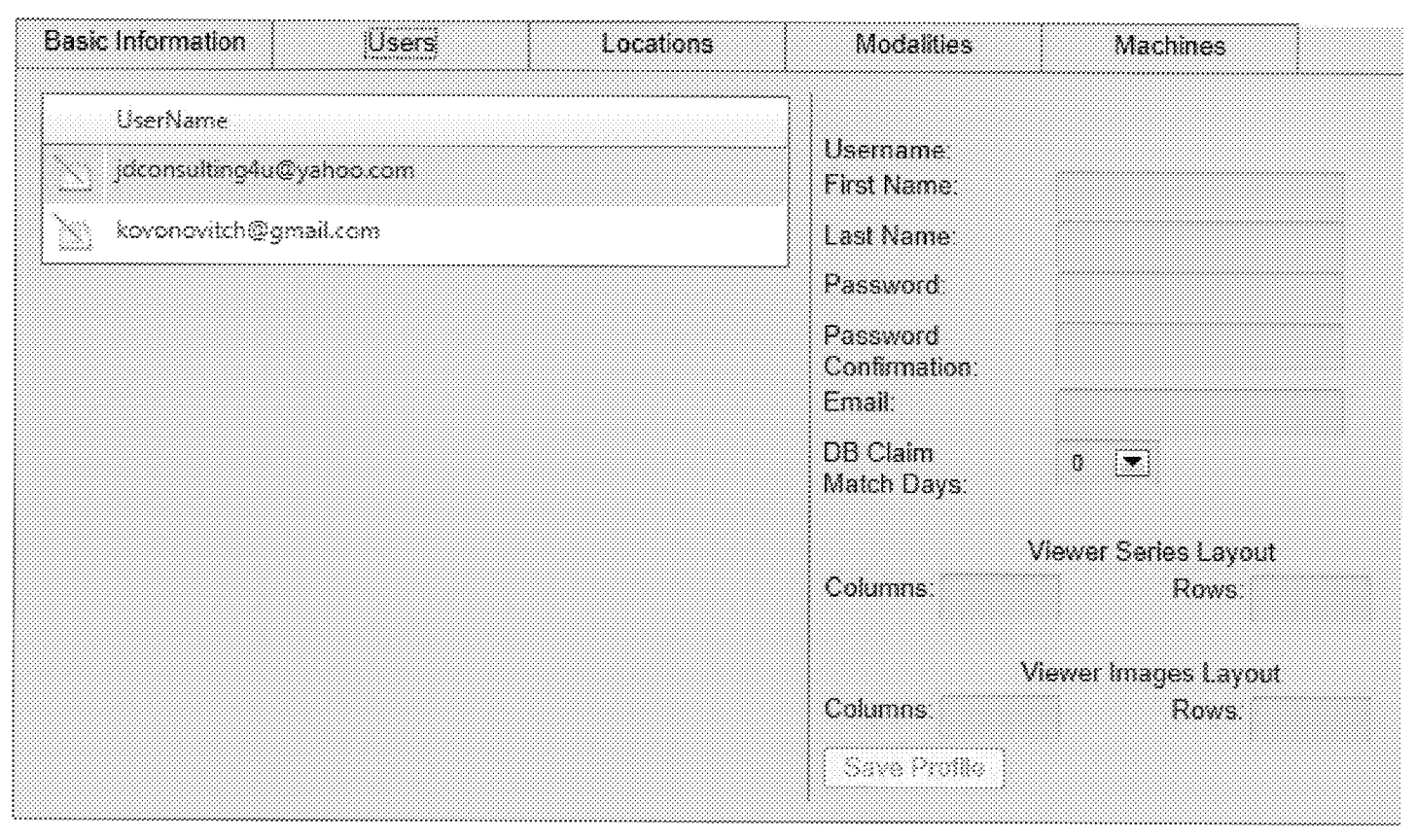

FIGS. 13-16 are exemplary screen shots illustrating various functions of the provider administration functions;

FIGS. 17-29 are exemplary screen shots illustrating how various functions of the present disclosure can be performed;

Figure 30:
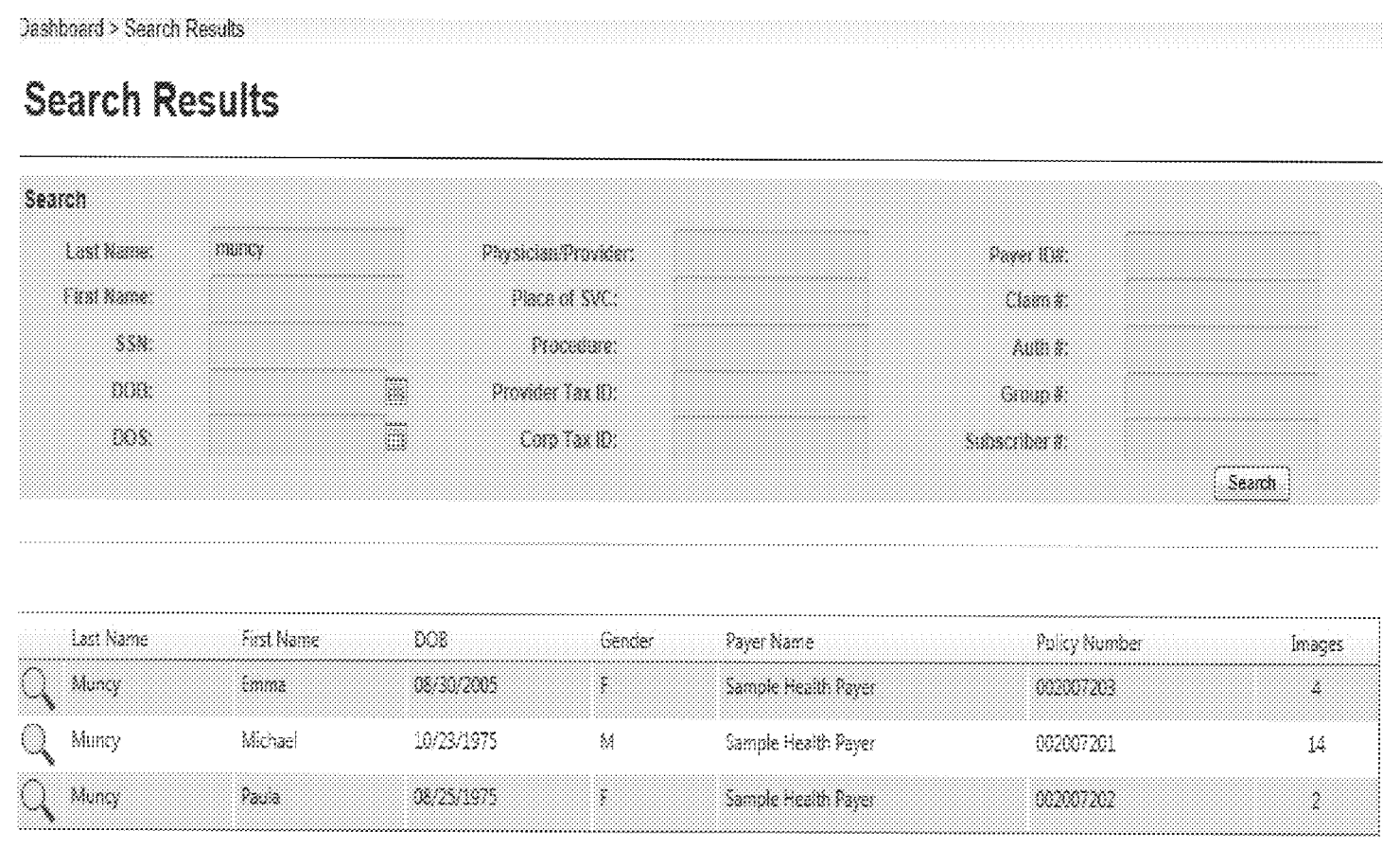
Figure 31:
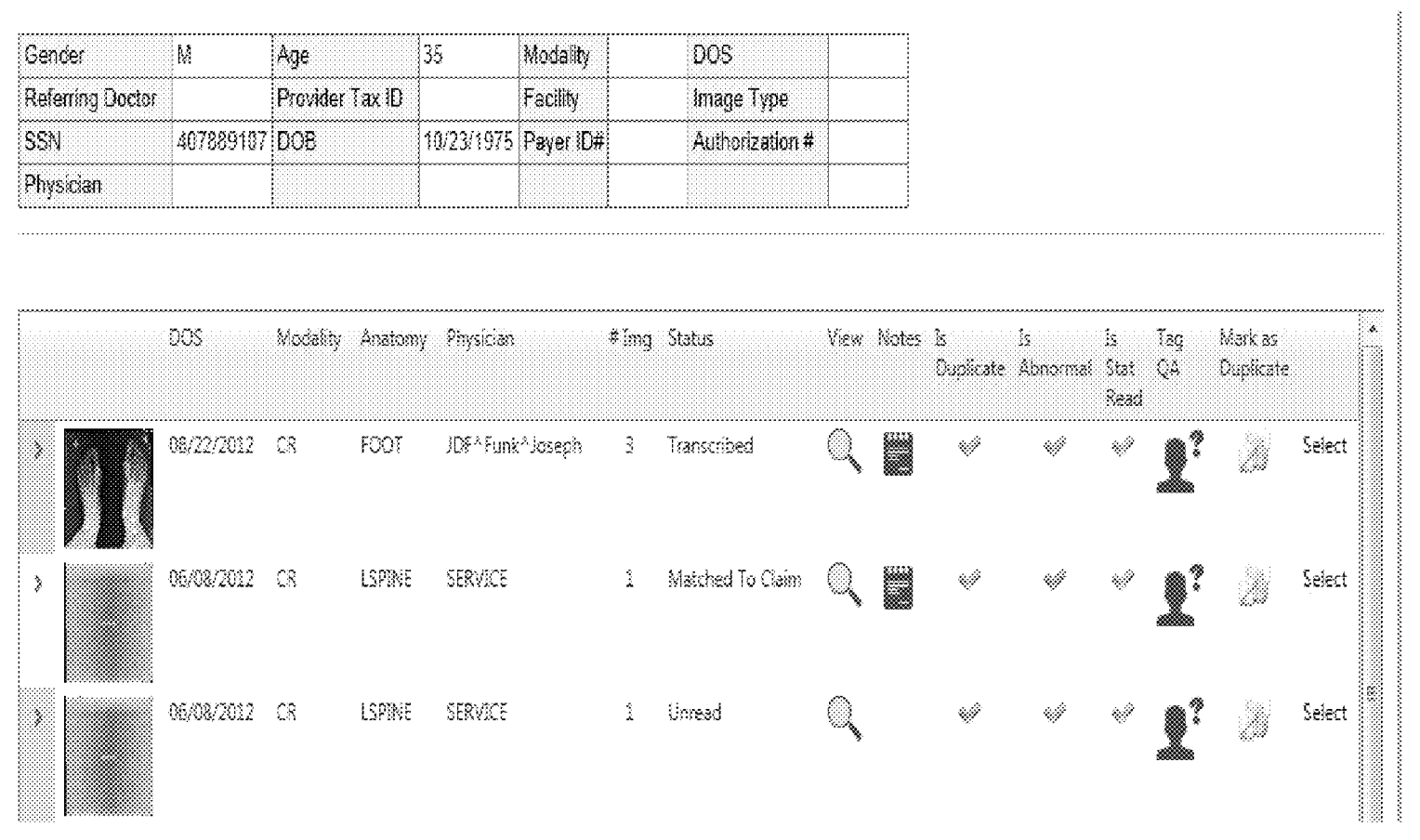

FIGS. 30-36 are exemplary screen shots illustrating how various searching functions of the present disclosure are performed;

Figure 37:
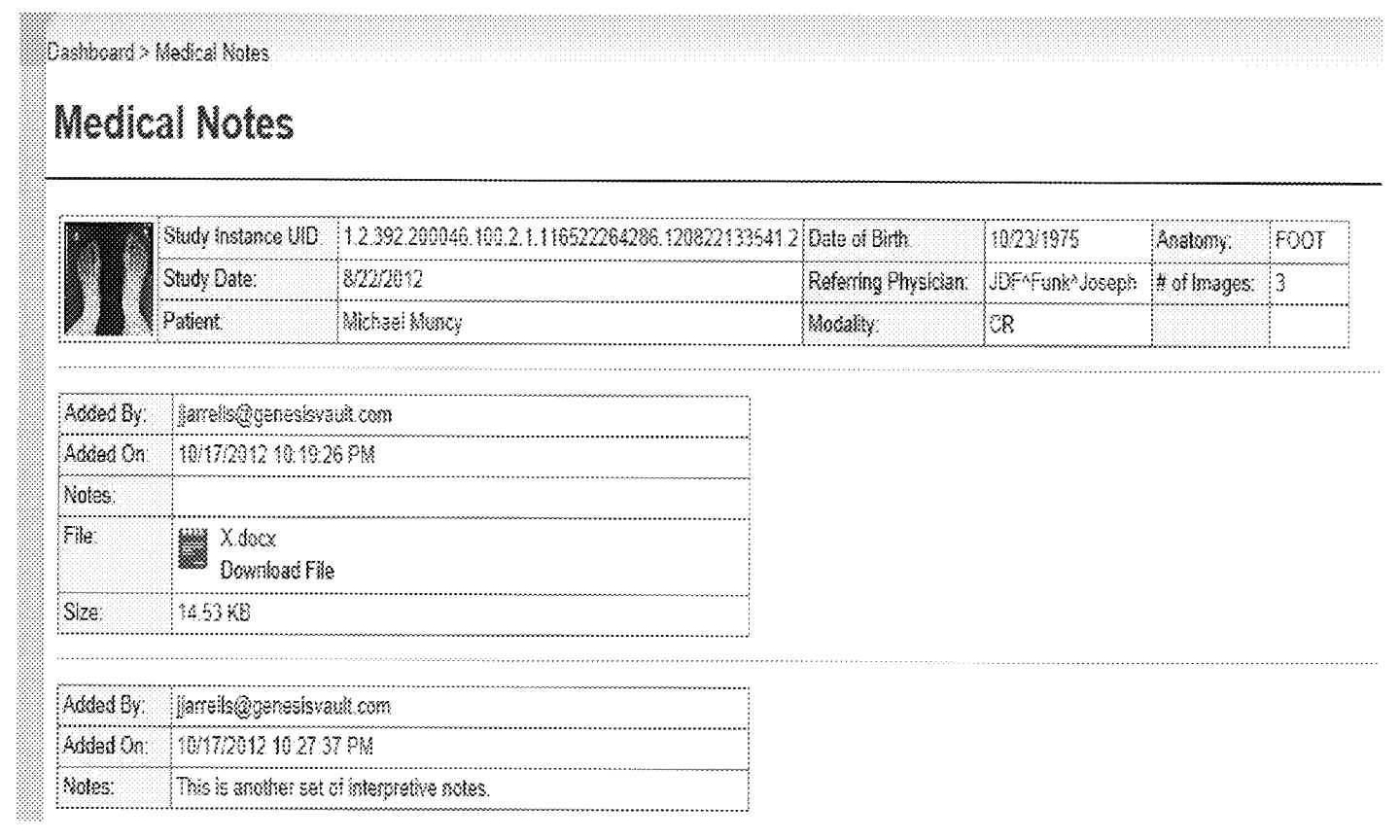

FIG. 37 is an exemplary screen shot illustrating how medical notes are tracked for each patient;

Figure 39:
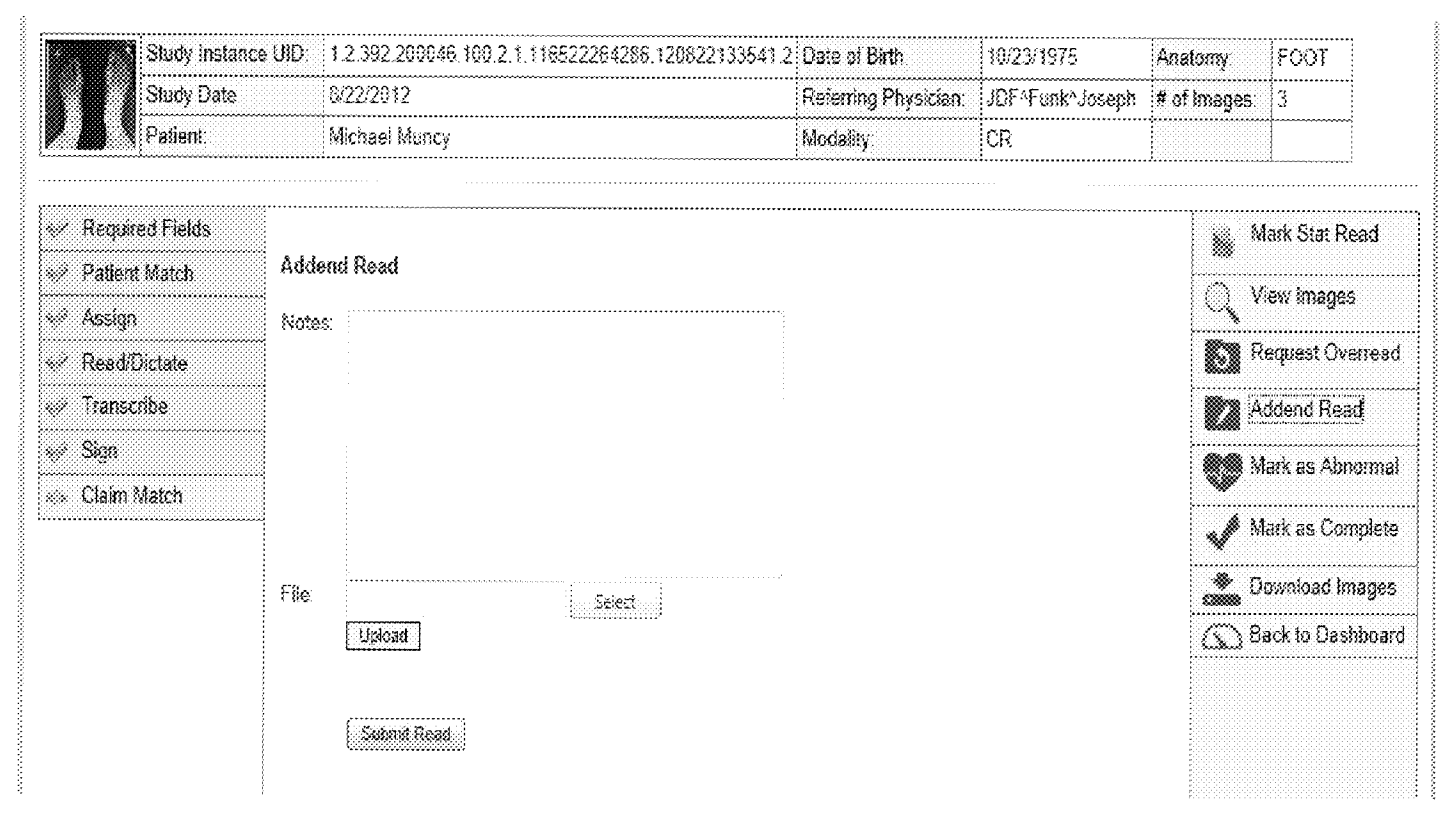

FIGS. 38-39 are exemplary screen shots illustrating how various functions of a tag study is performed by the present disclosure;

Figure 40:
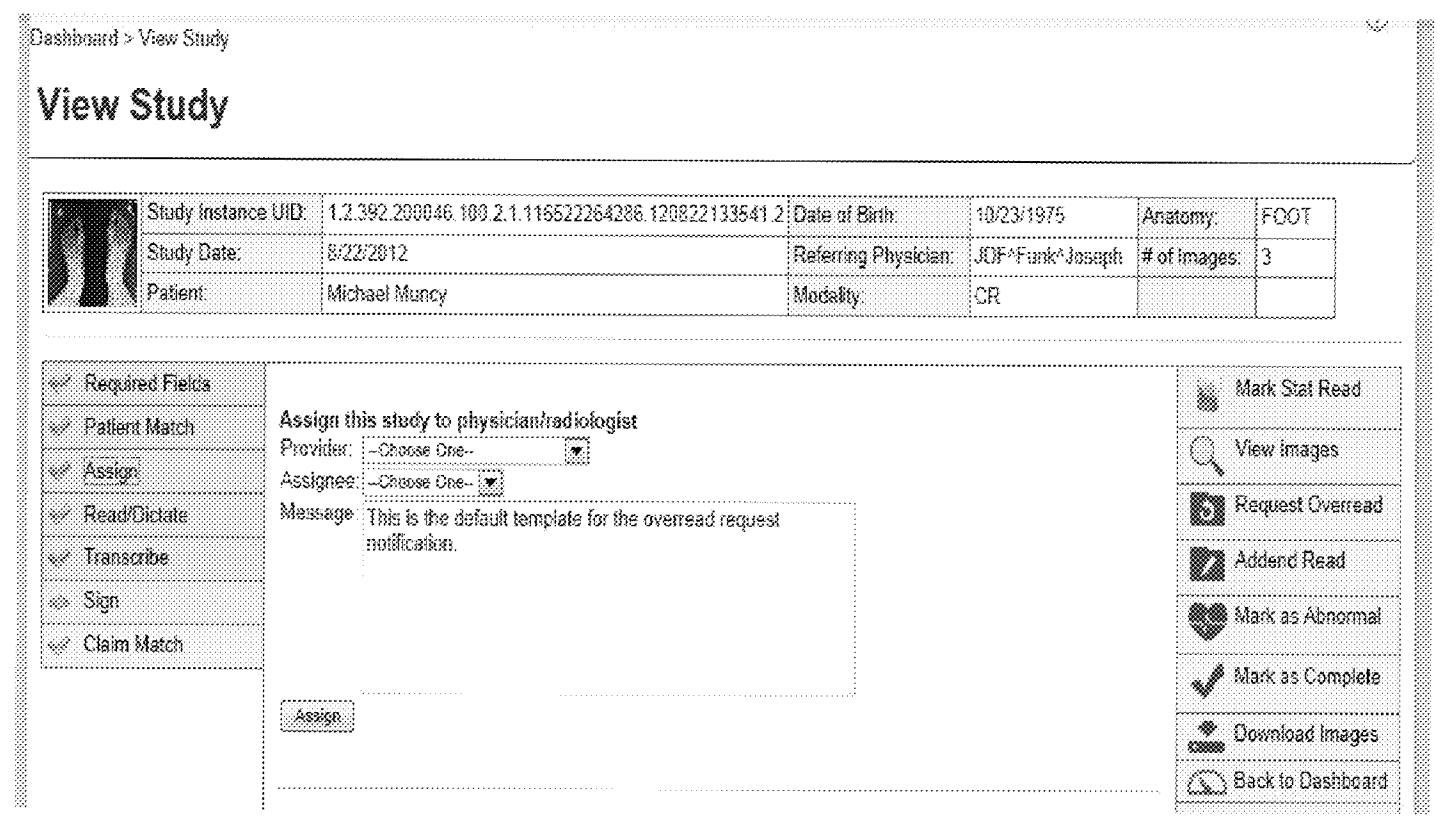
Figure 42:
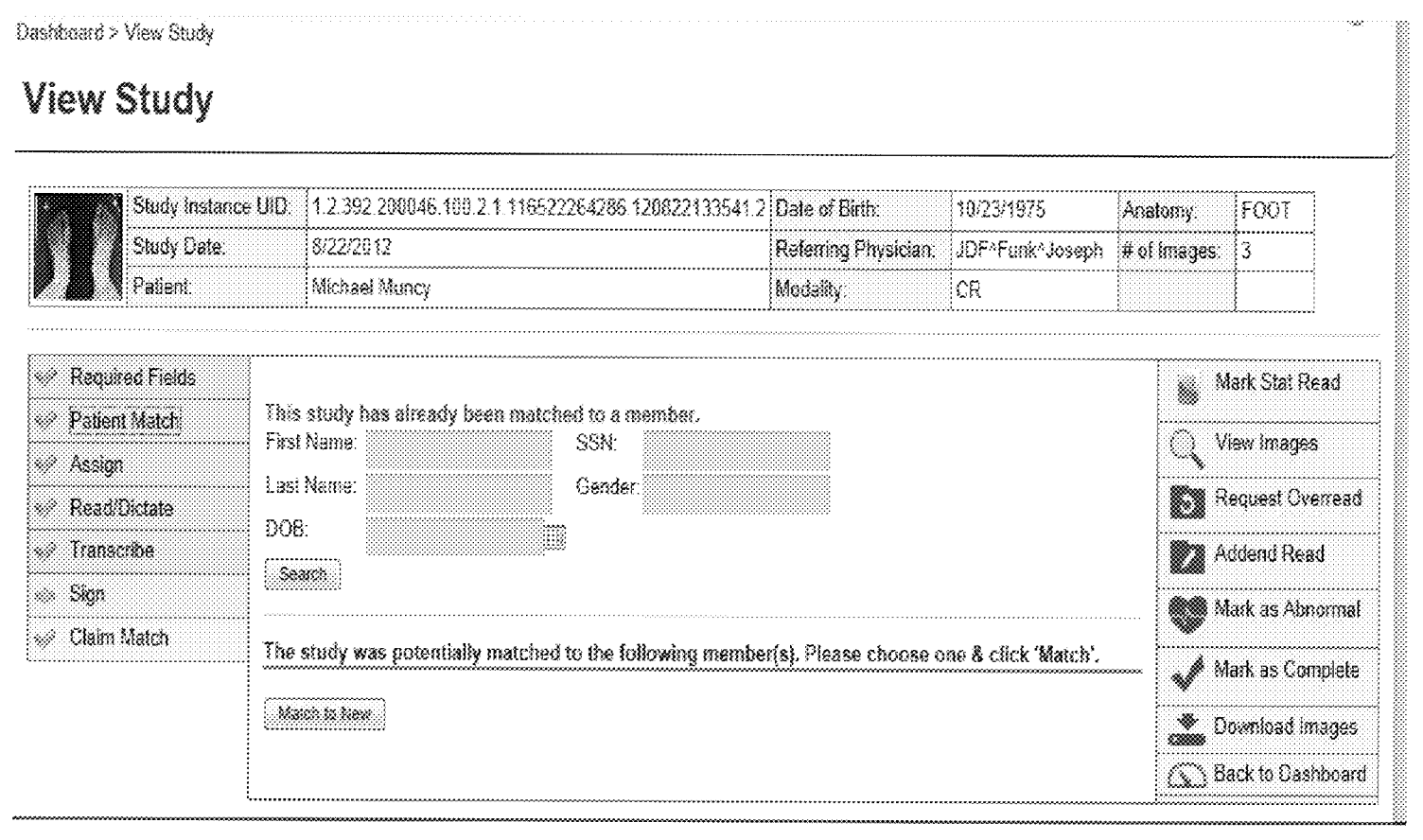
Figure 43:
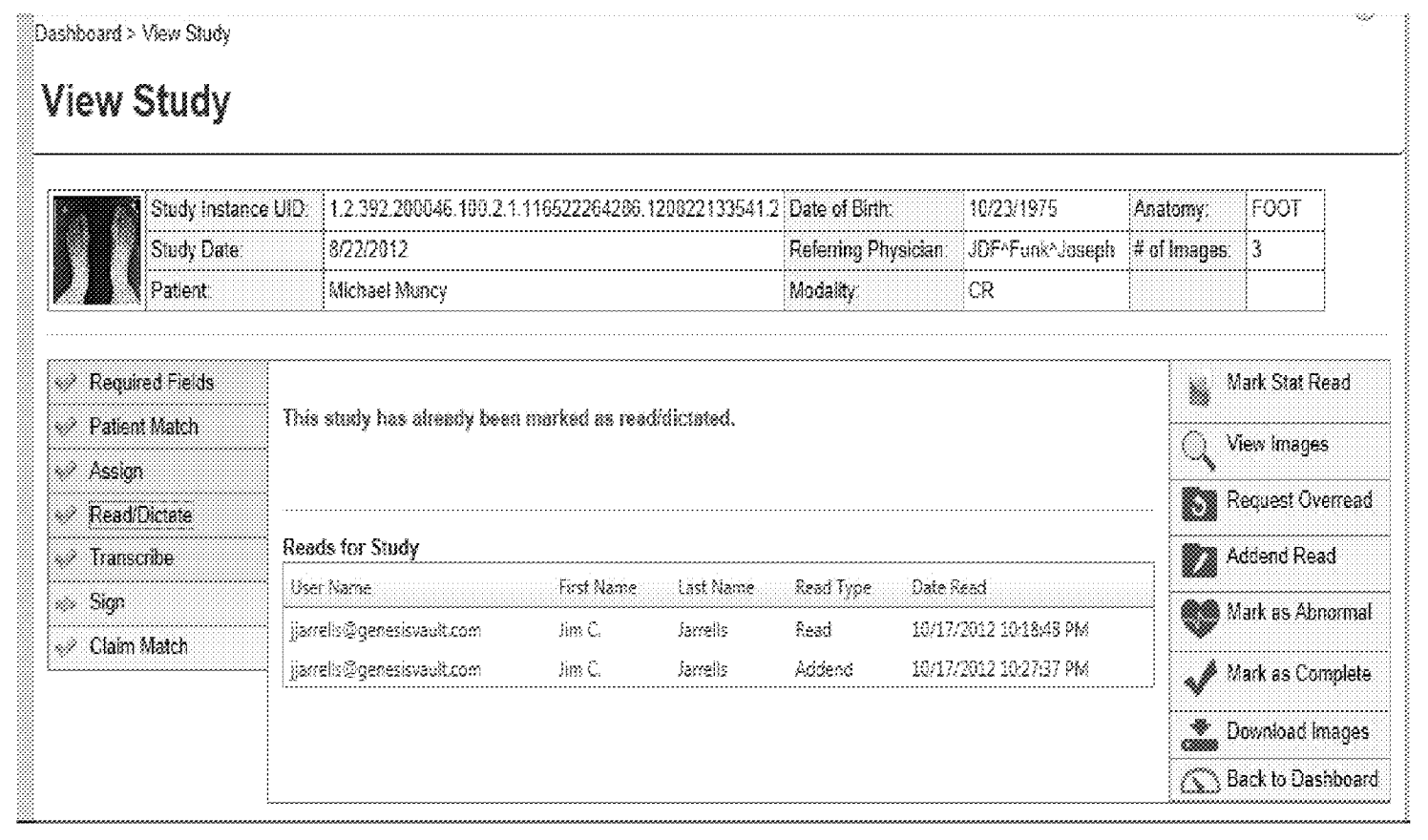
Figure 44:
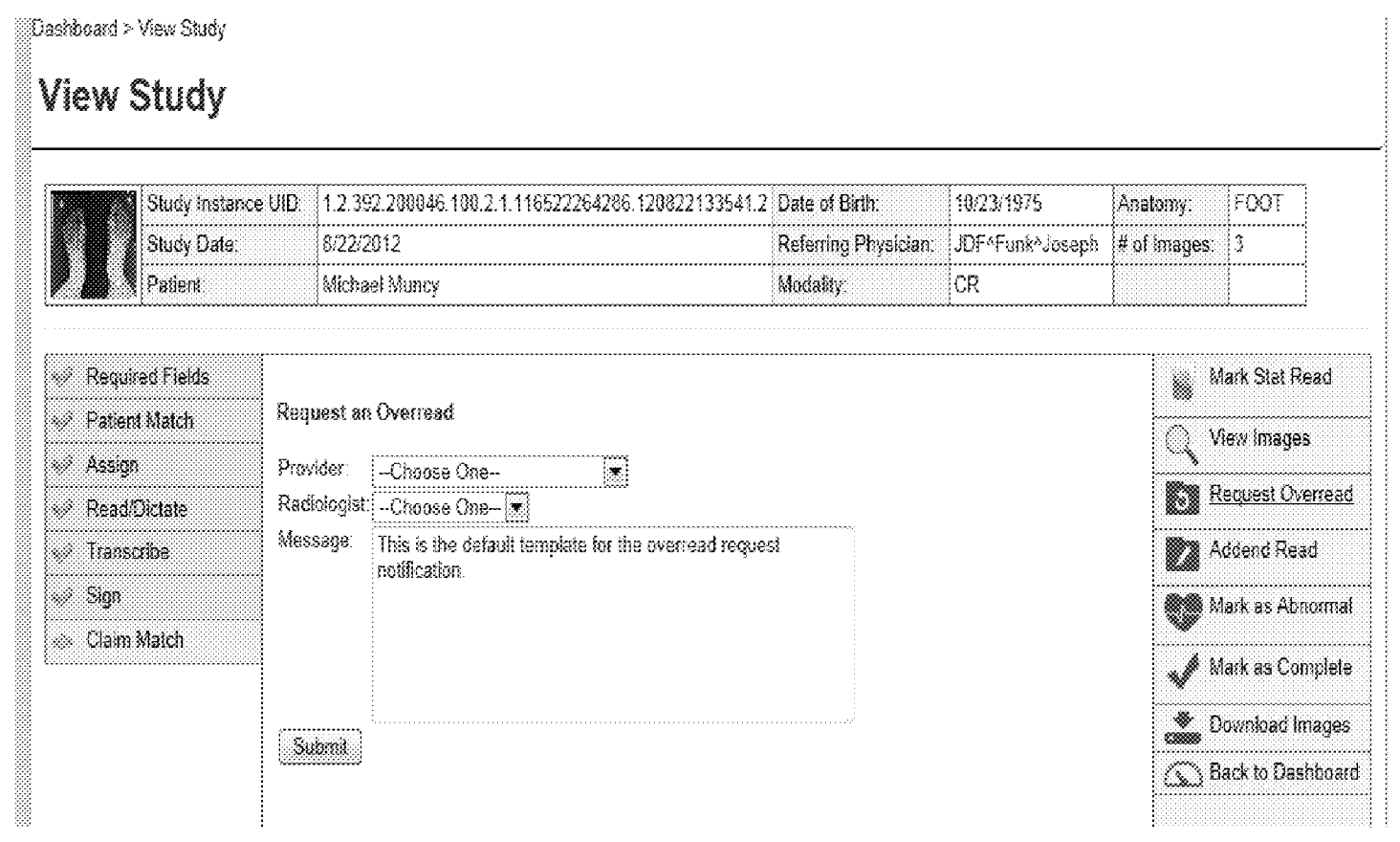
Figure 45:
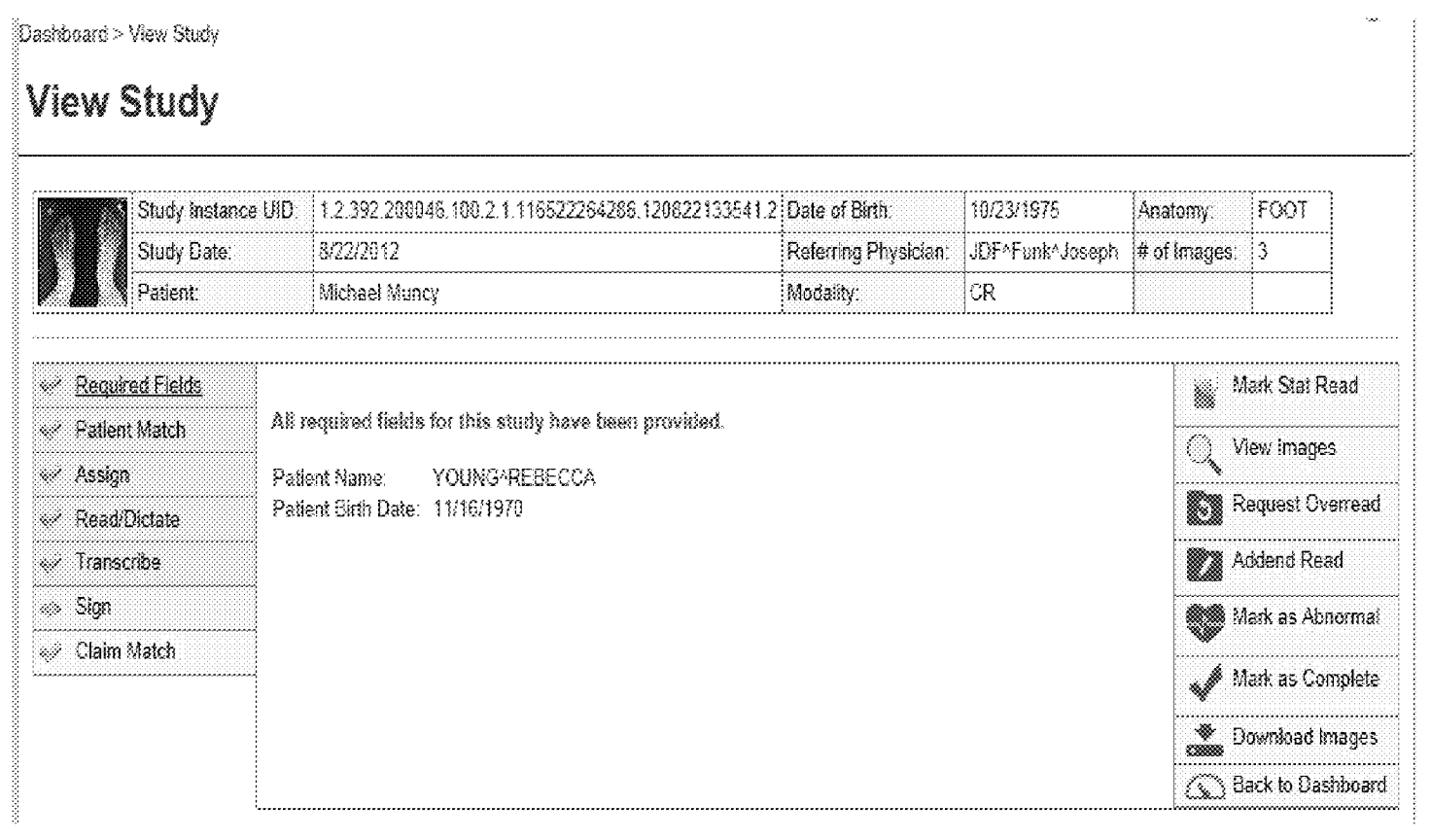

FIGS. 40-47 are exemplary screen shots illustrating how various functions of a view study is performed by the present disclosure;

FIG. 48 is an exemplary screen shots illustrating how a user can manage his/her profile.

DETAILED DESCRIPTION OF THE DISCLOSURE

Figure 1:
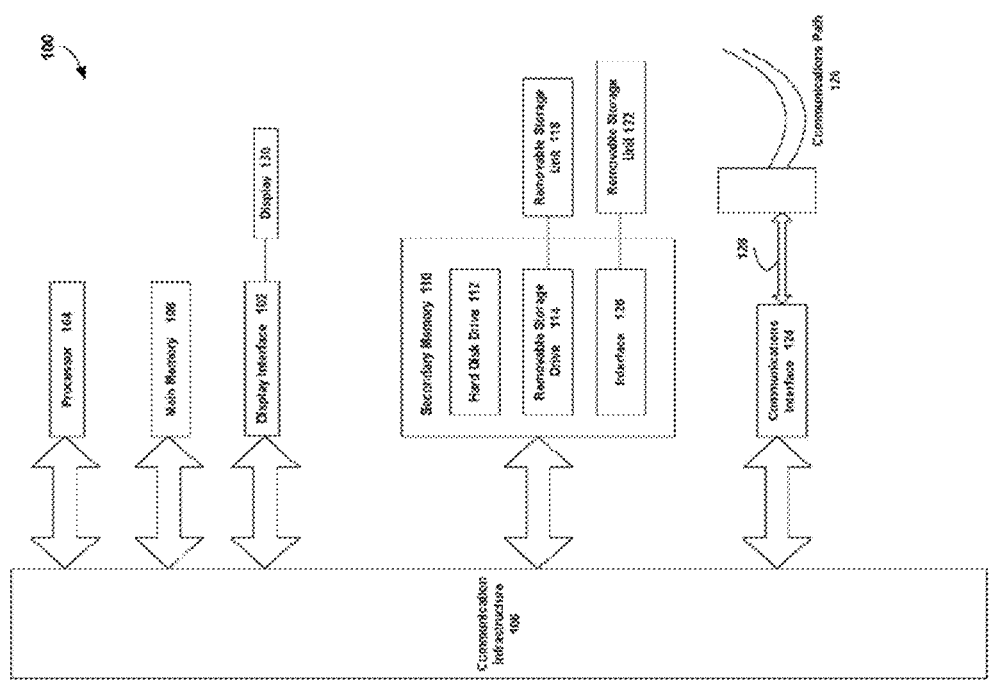
FIG. 1 is high level schematic block diagram illustrating the interrelationship between major components of an exemplary computing device capable of performing the functions of the present disclosure.
Figure 2:
FIG. 2 provides an overview of the logical data flow from the study receipt into the system through the end of the process. This represents a high level data flow of the entirety of the system from the radiology image/study point of view.
Figure 3:
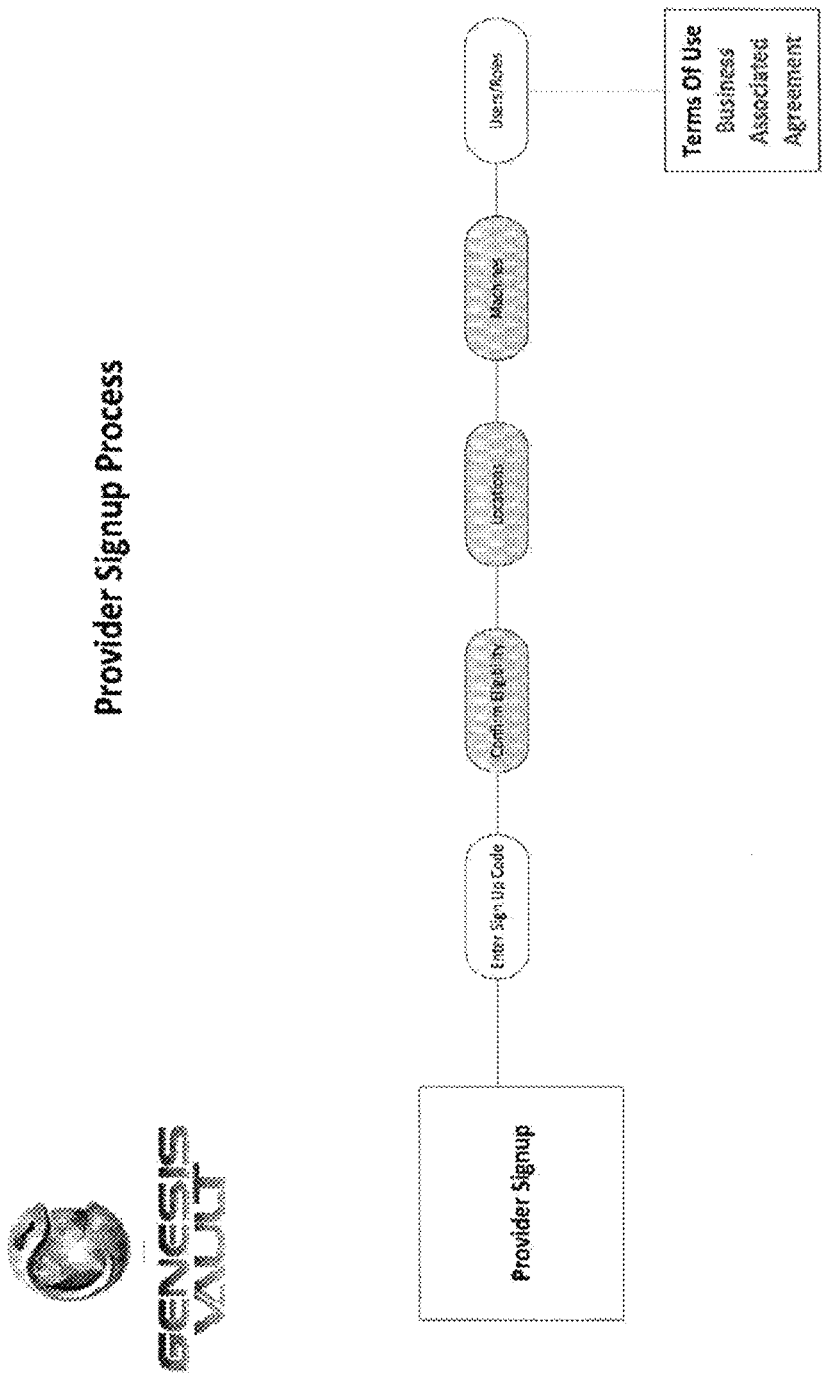
FIG. 3.
Figure 4:
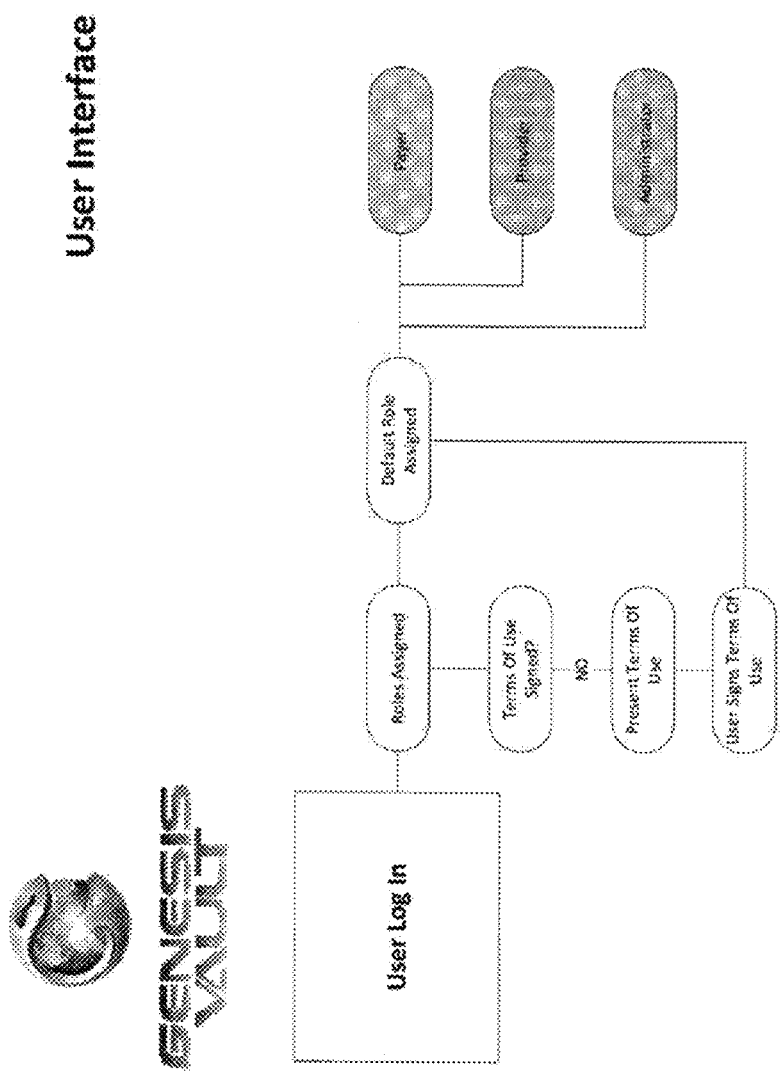
FIG. 4.
Figure 5:
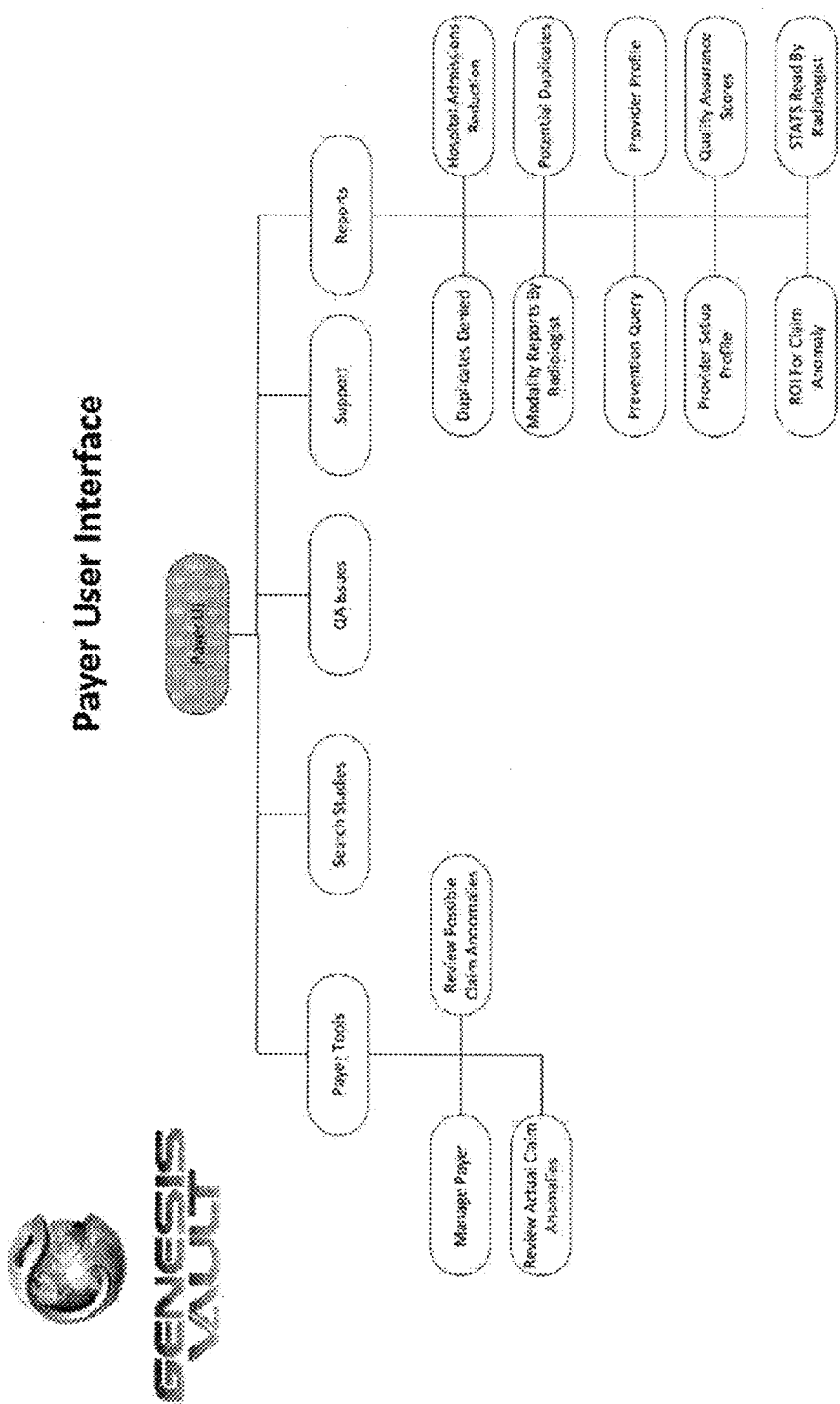
FIG. 5.
Figure 6:
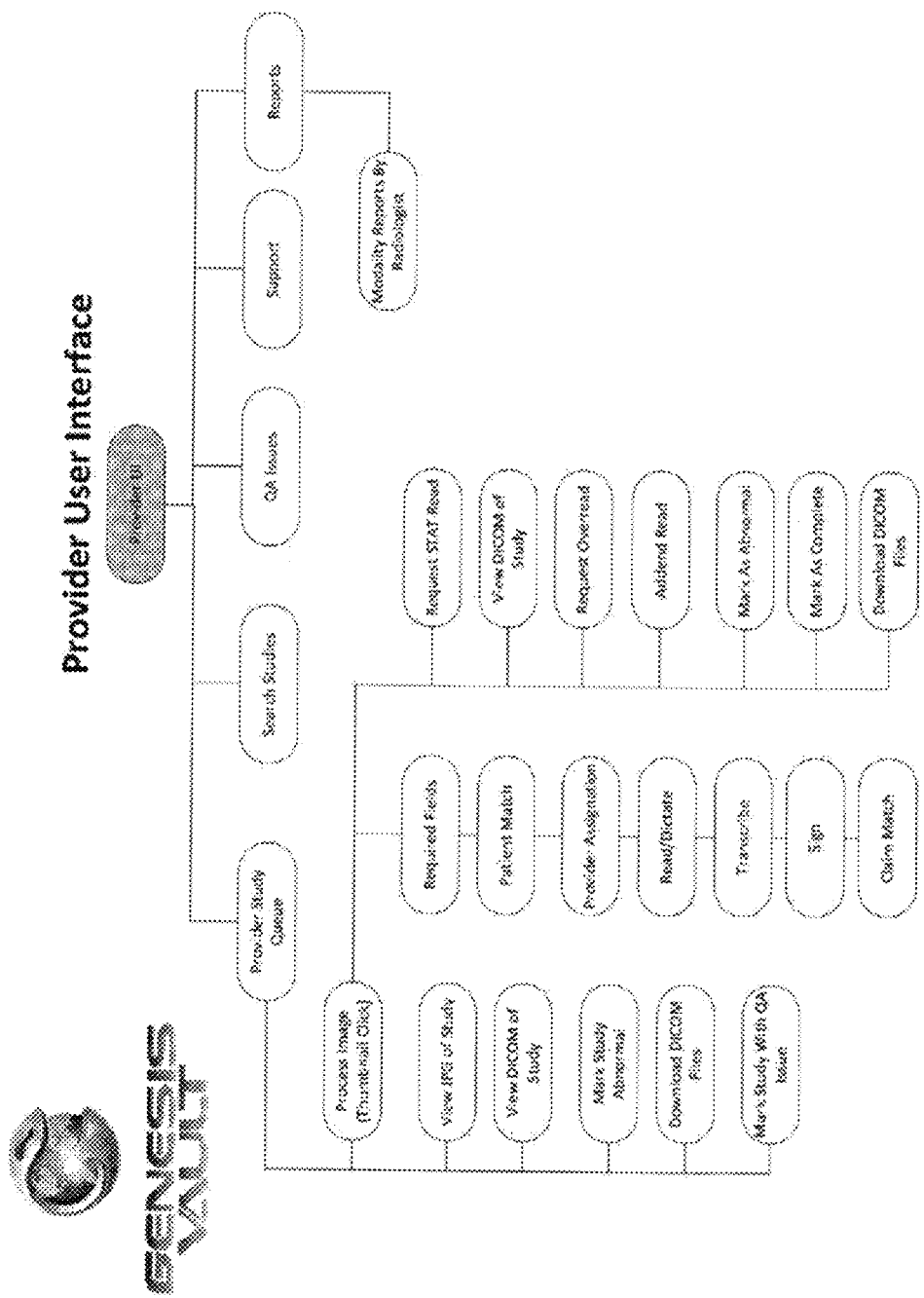
FIG. 6.
Figure 7:
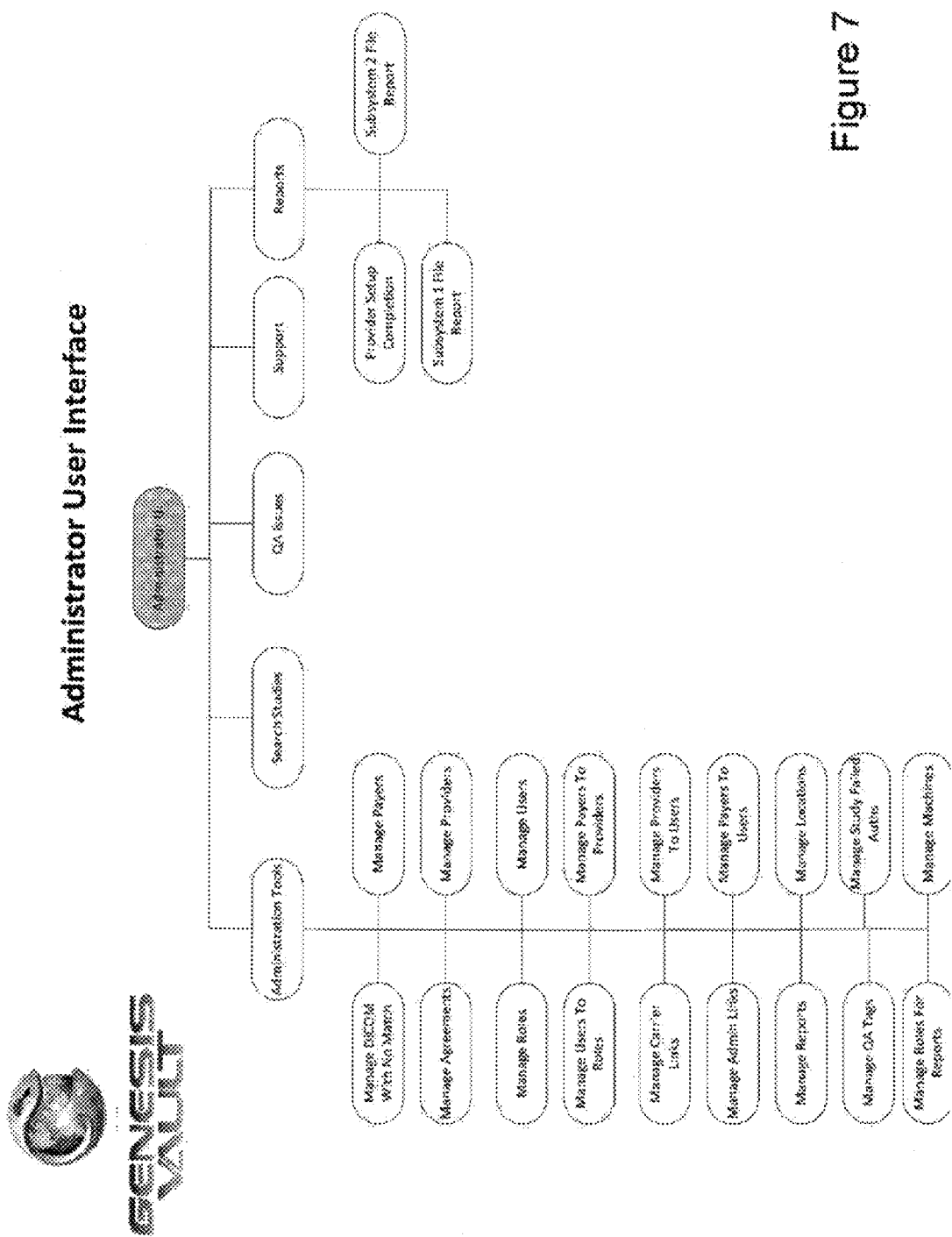
FIG. 7.
Figure 8:
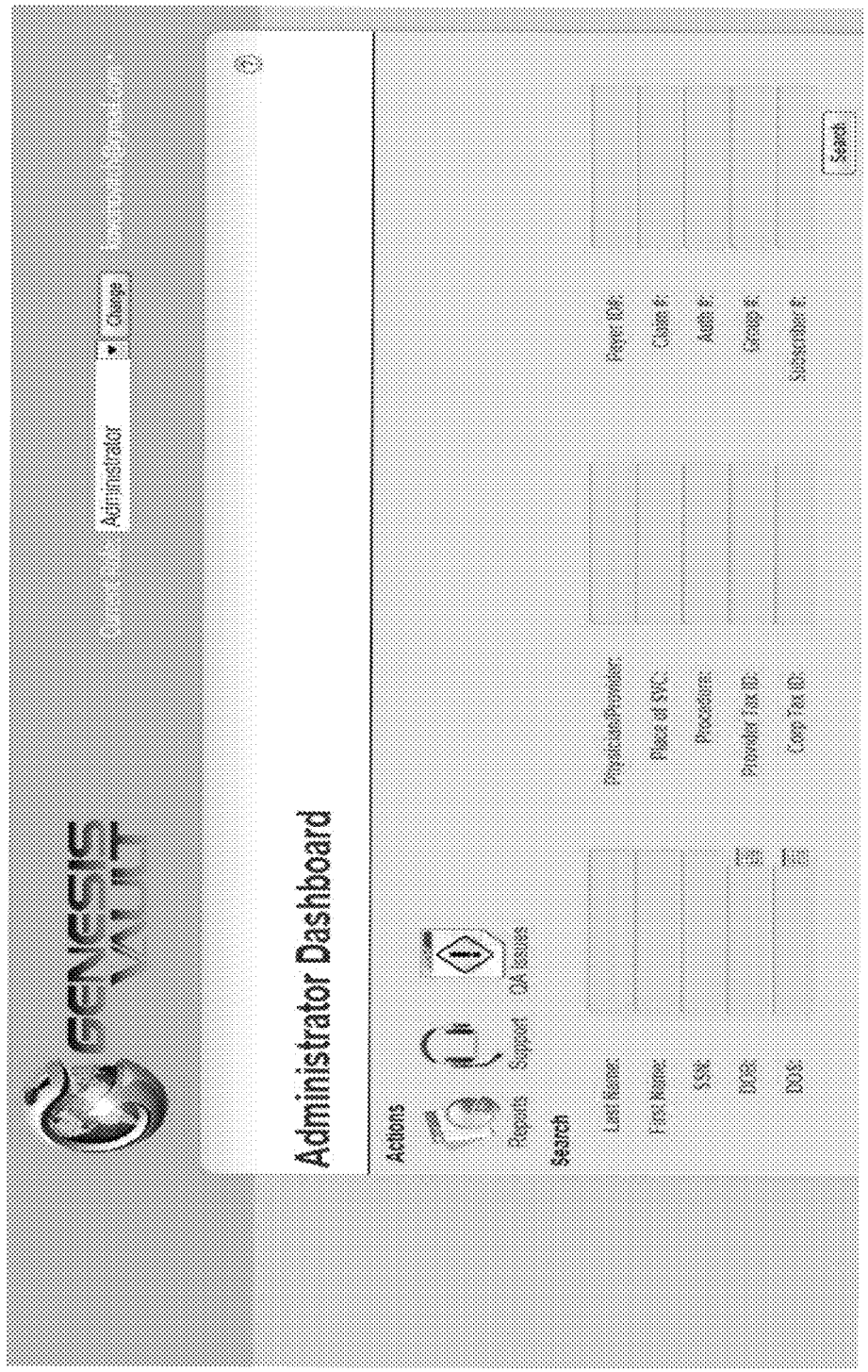
FIG. 8 displays the claim match screen for an image/study as well as the Administrator Dashboard. The claim match screen displays the results of a claim match for that study in the system. The Administrator Dashboard is the default dashboard for administrative purposes.
Figure 9:
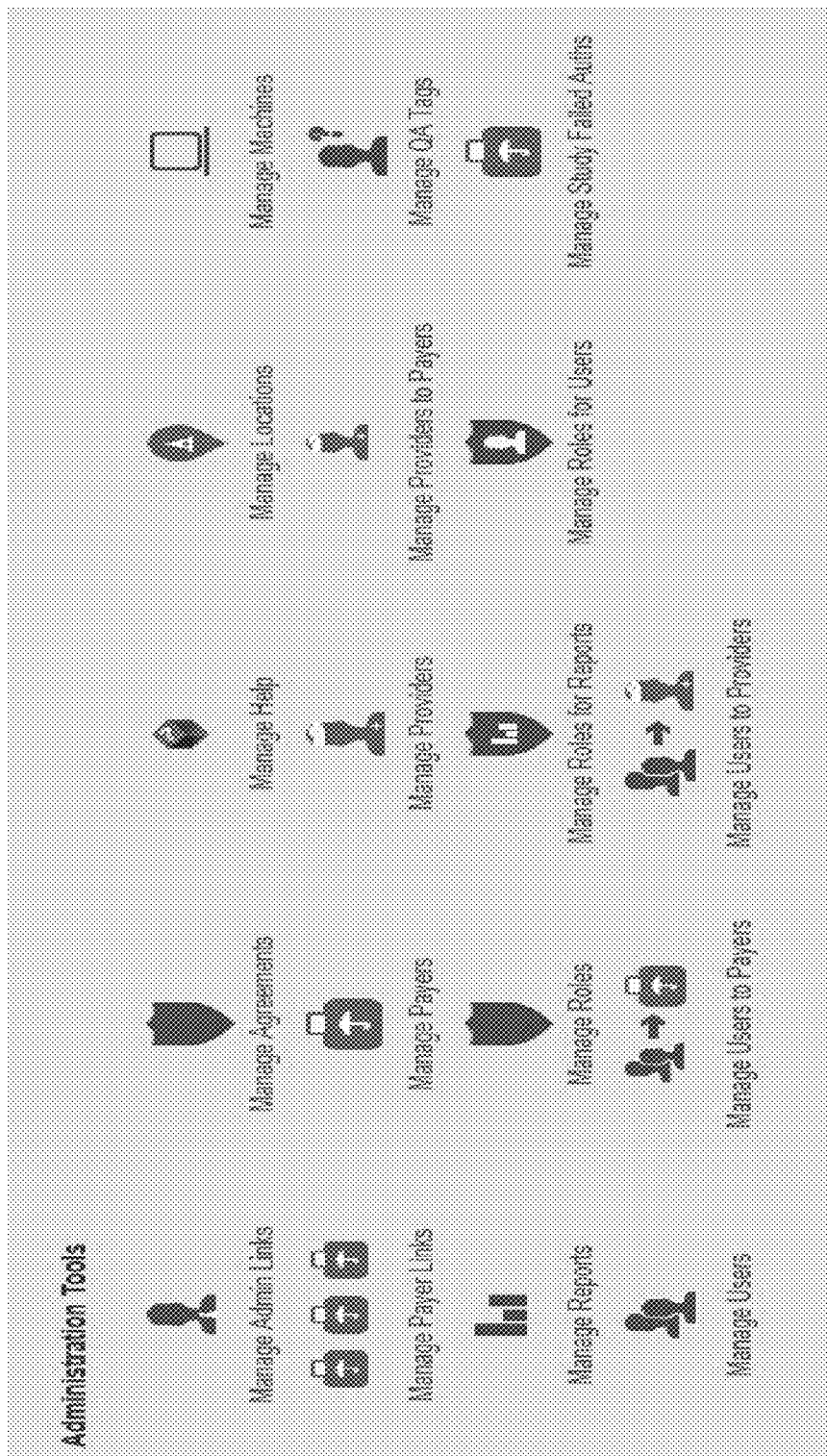
FIG. 9 displays links to administrative tools available to the administrator.
Figure 11:
Figure 15:
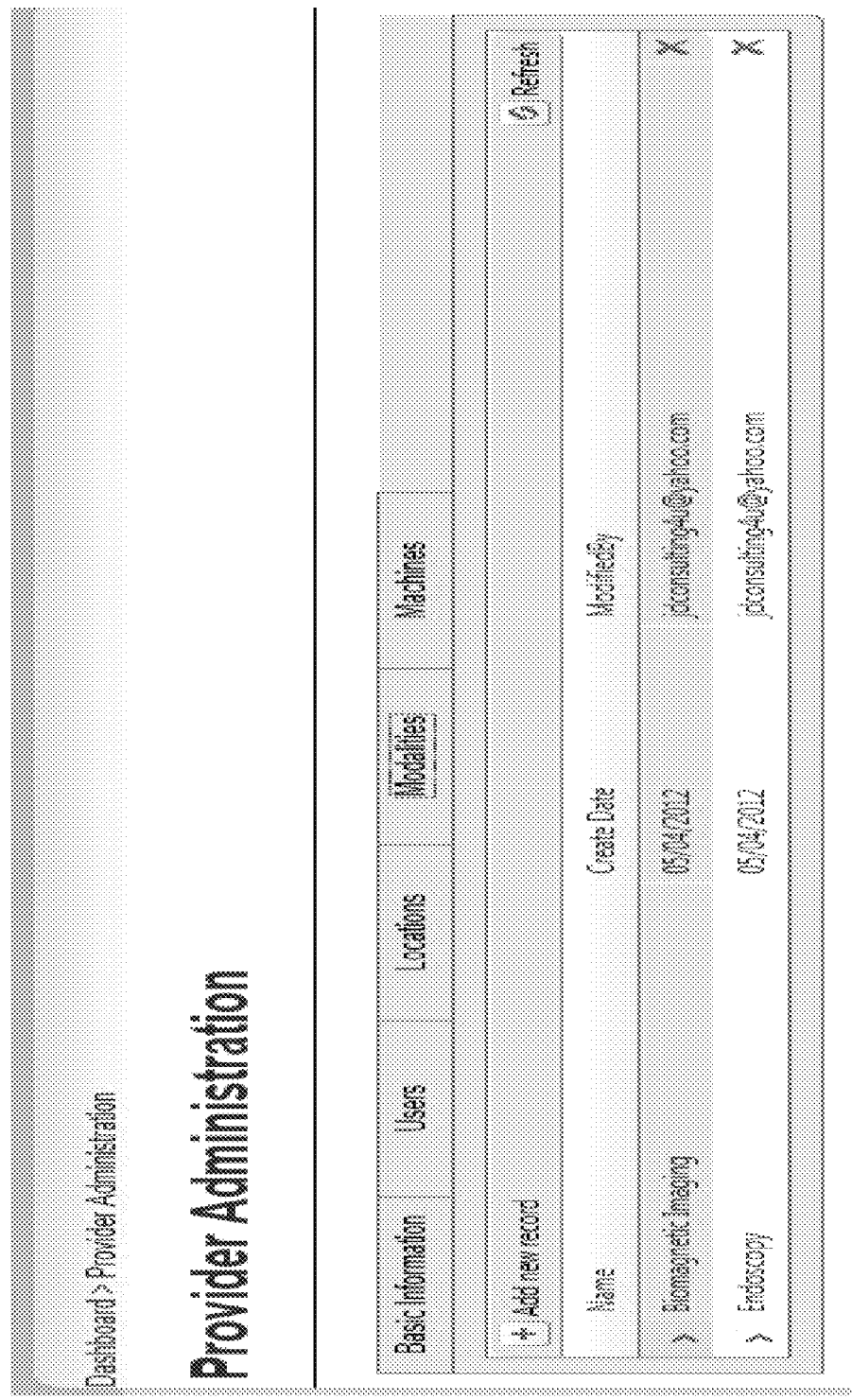
Figure 17:
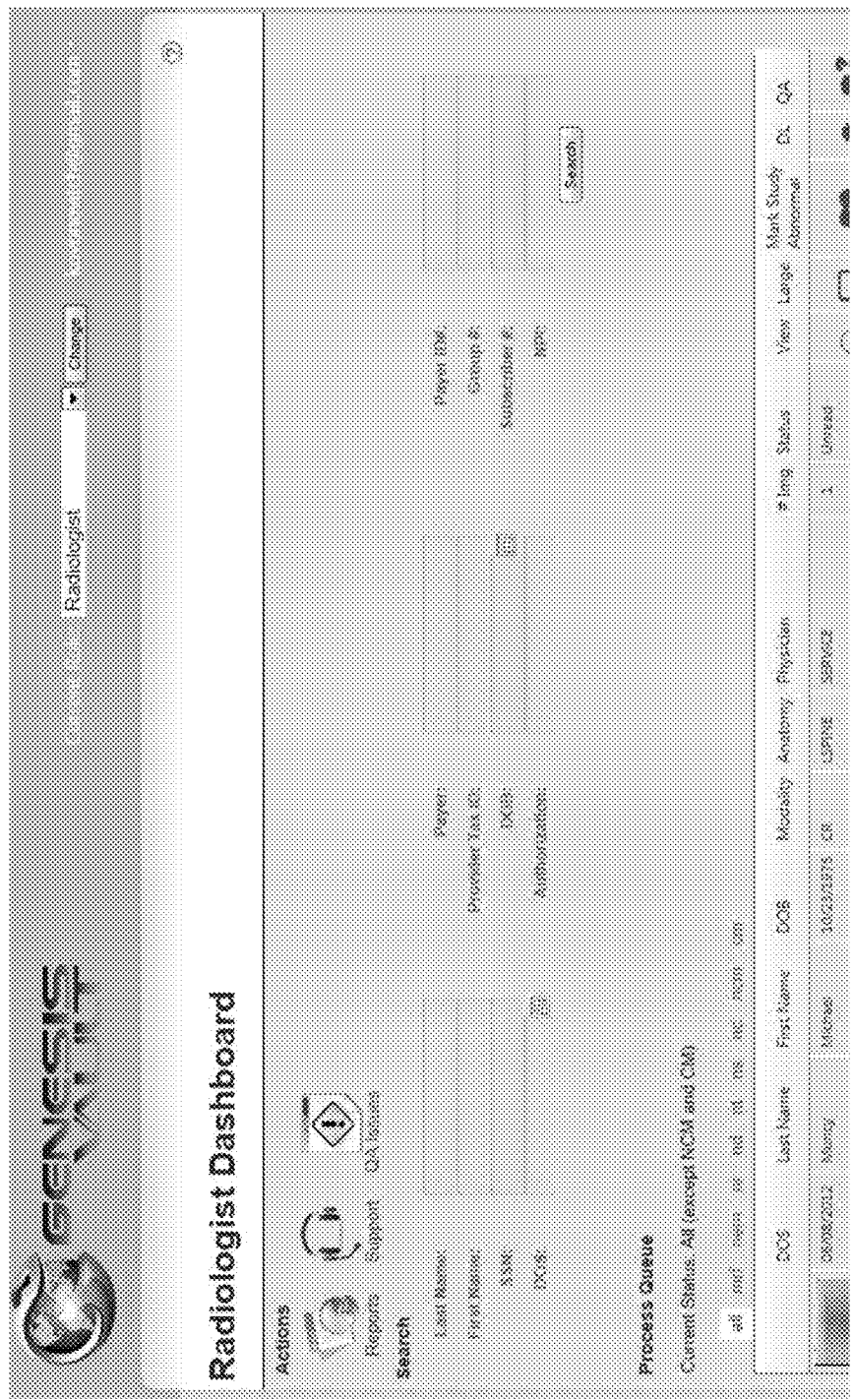
Figure 22:
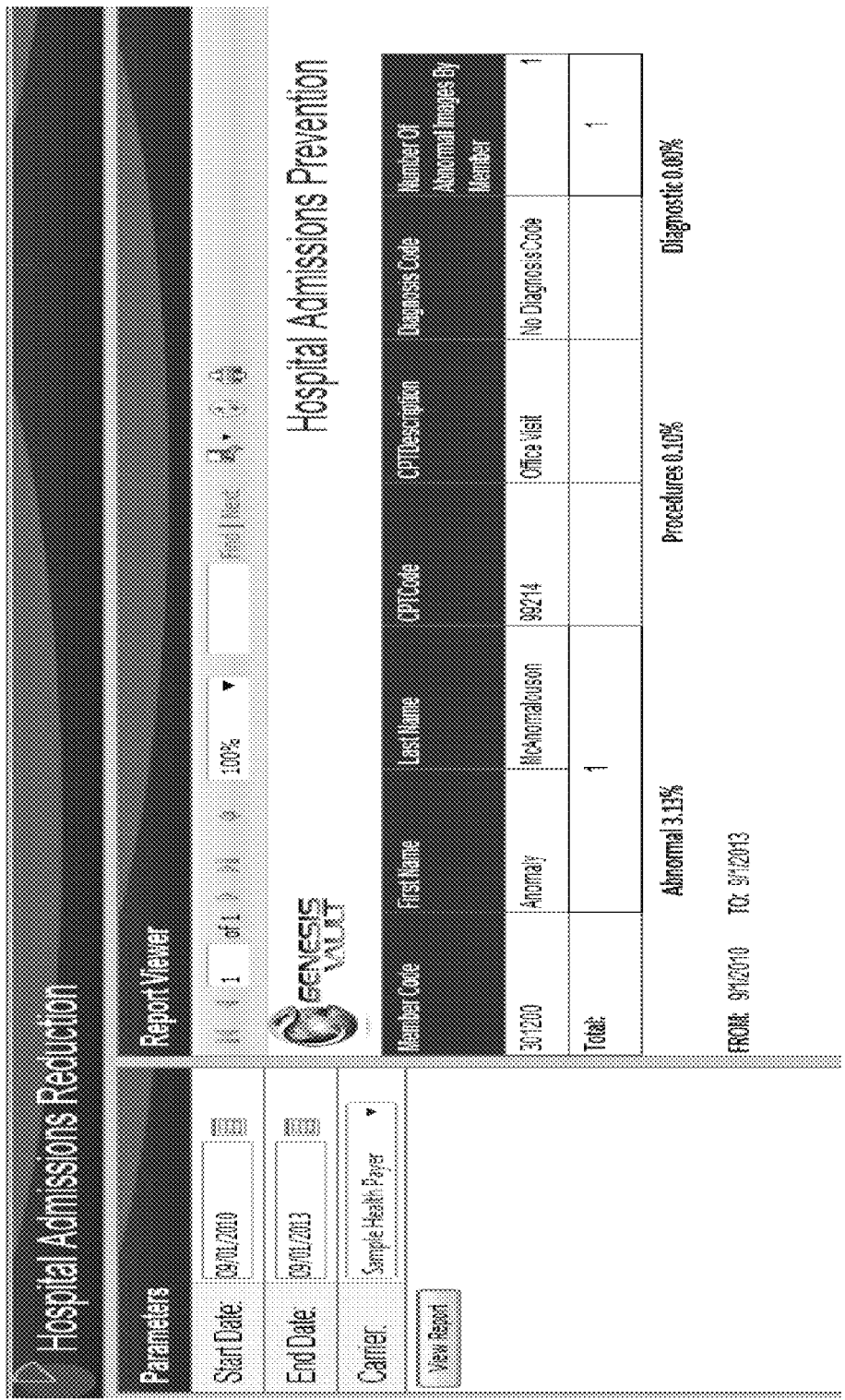
Figure 29:
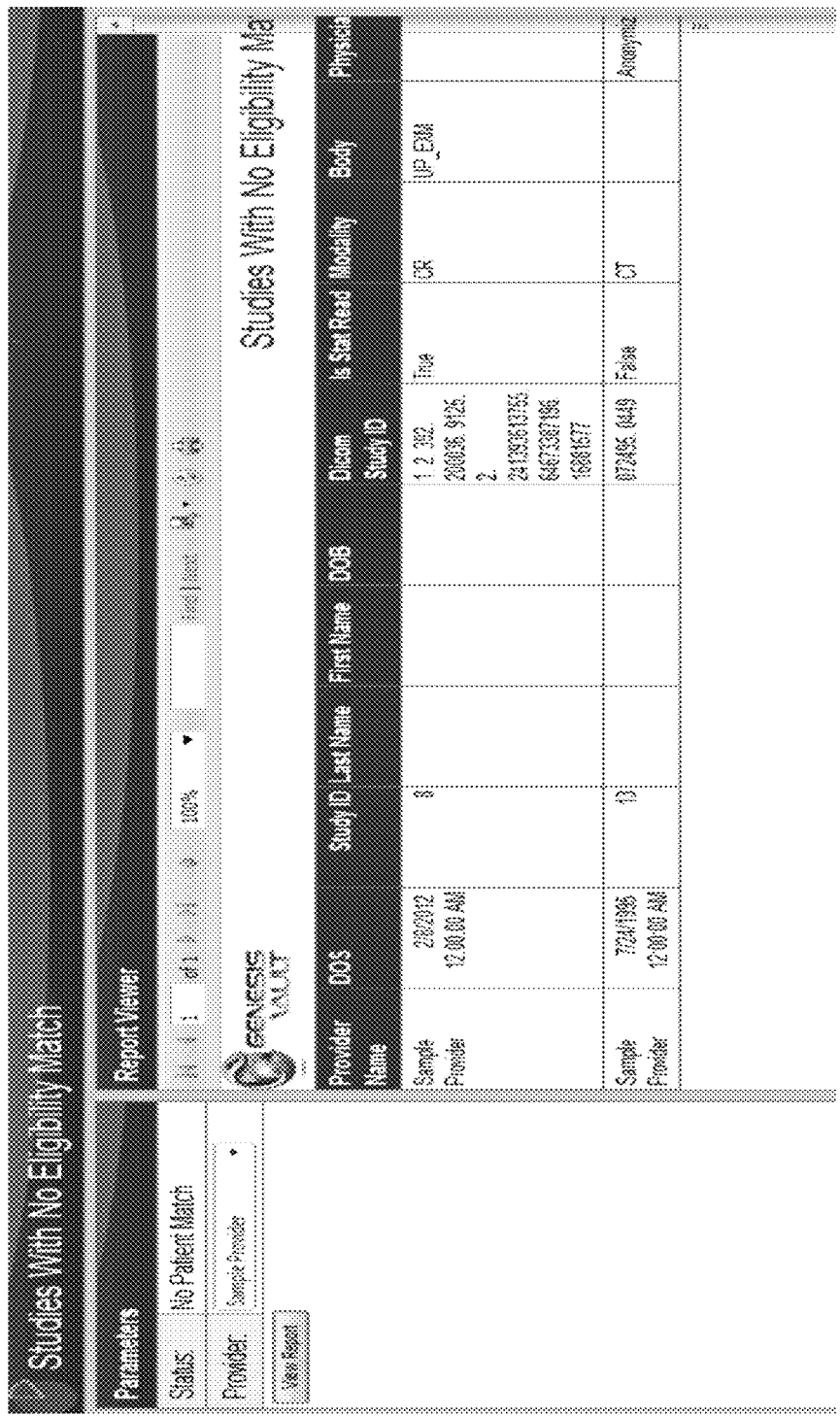
Figure 32:
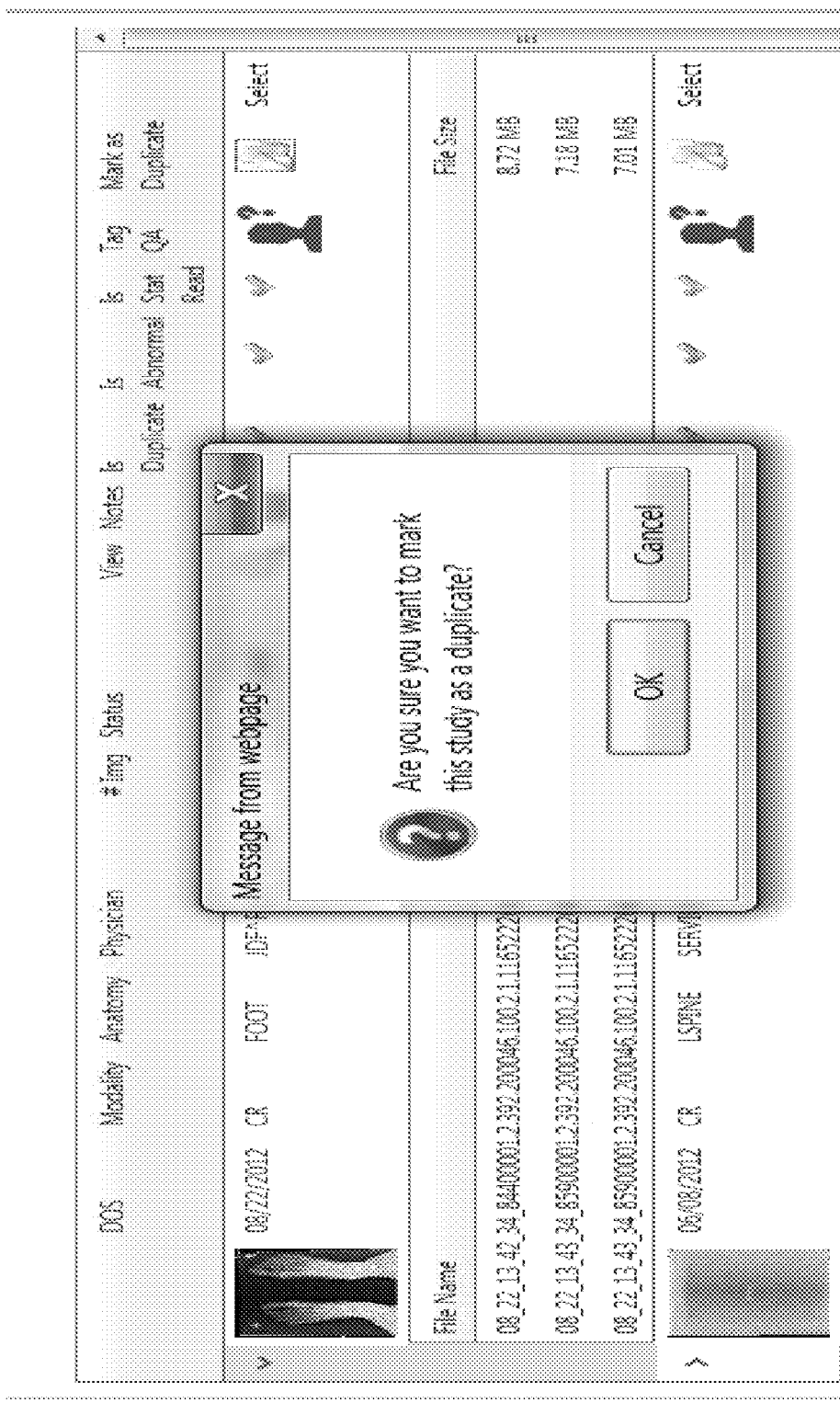
Figure 33:
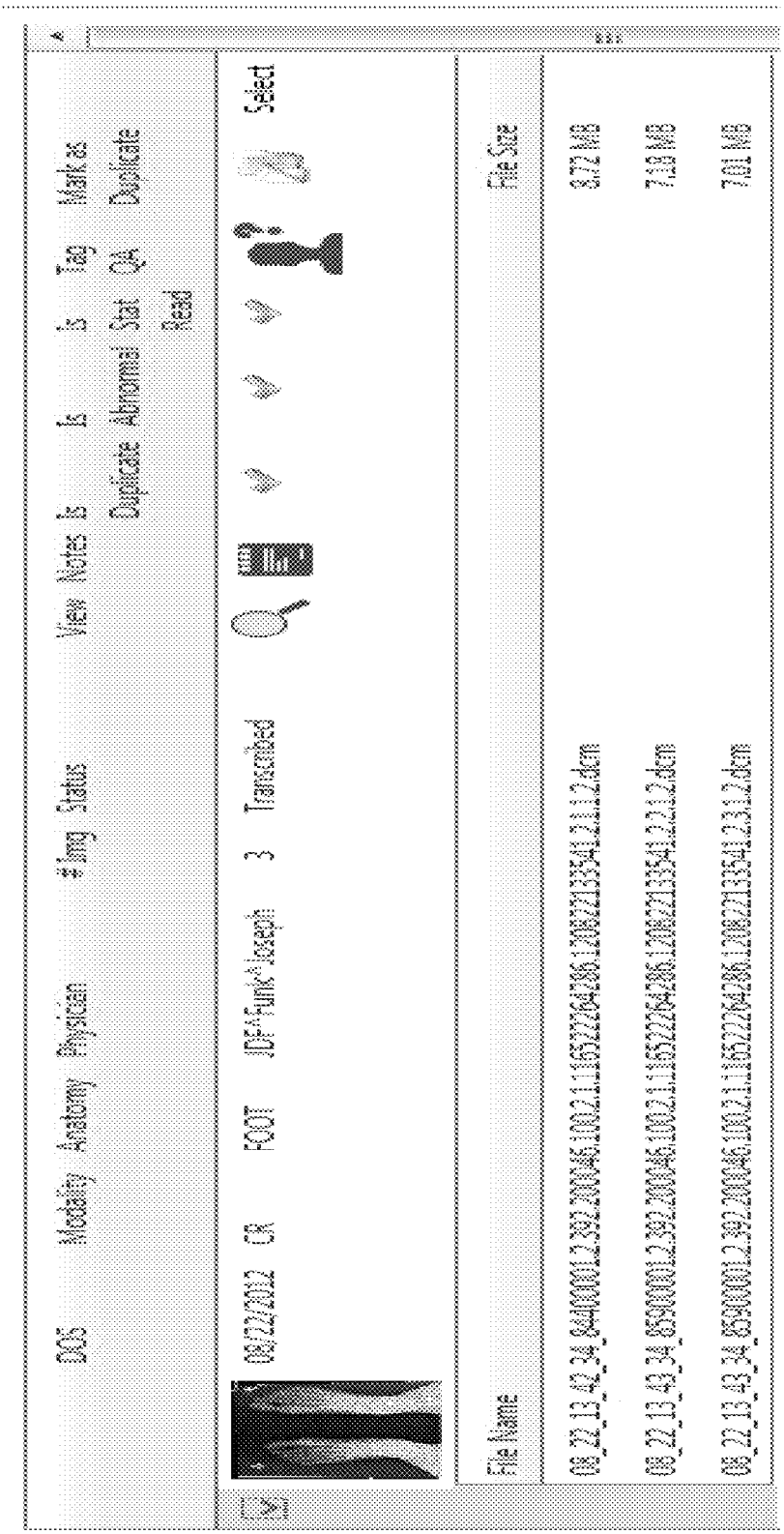
Figure 35:
Figure 36:
Figure 41:
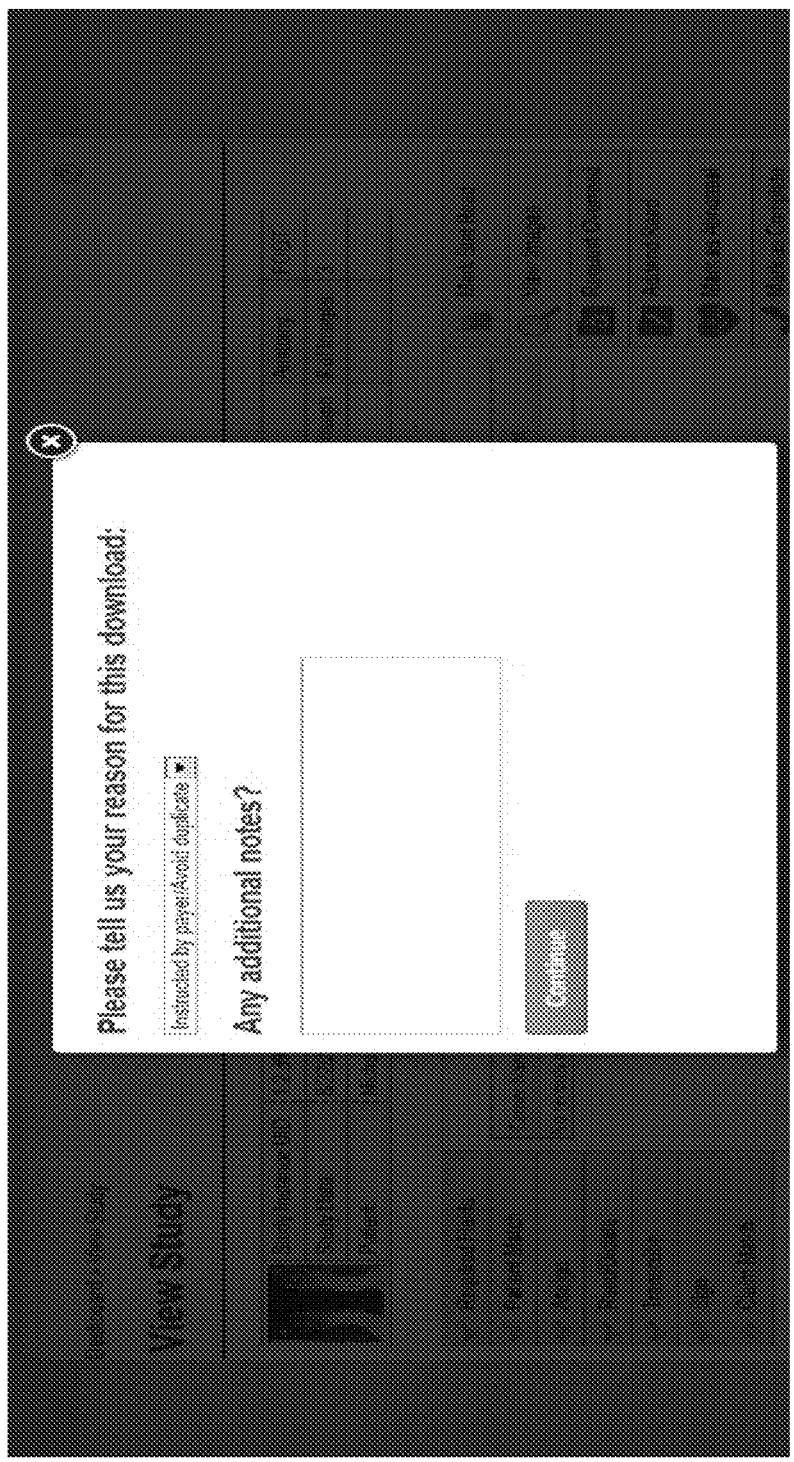
Figure 47:
Figure 49:
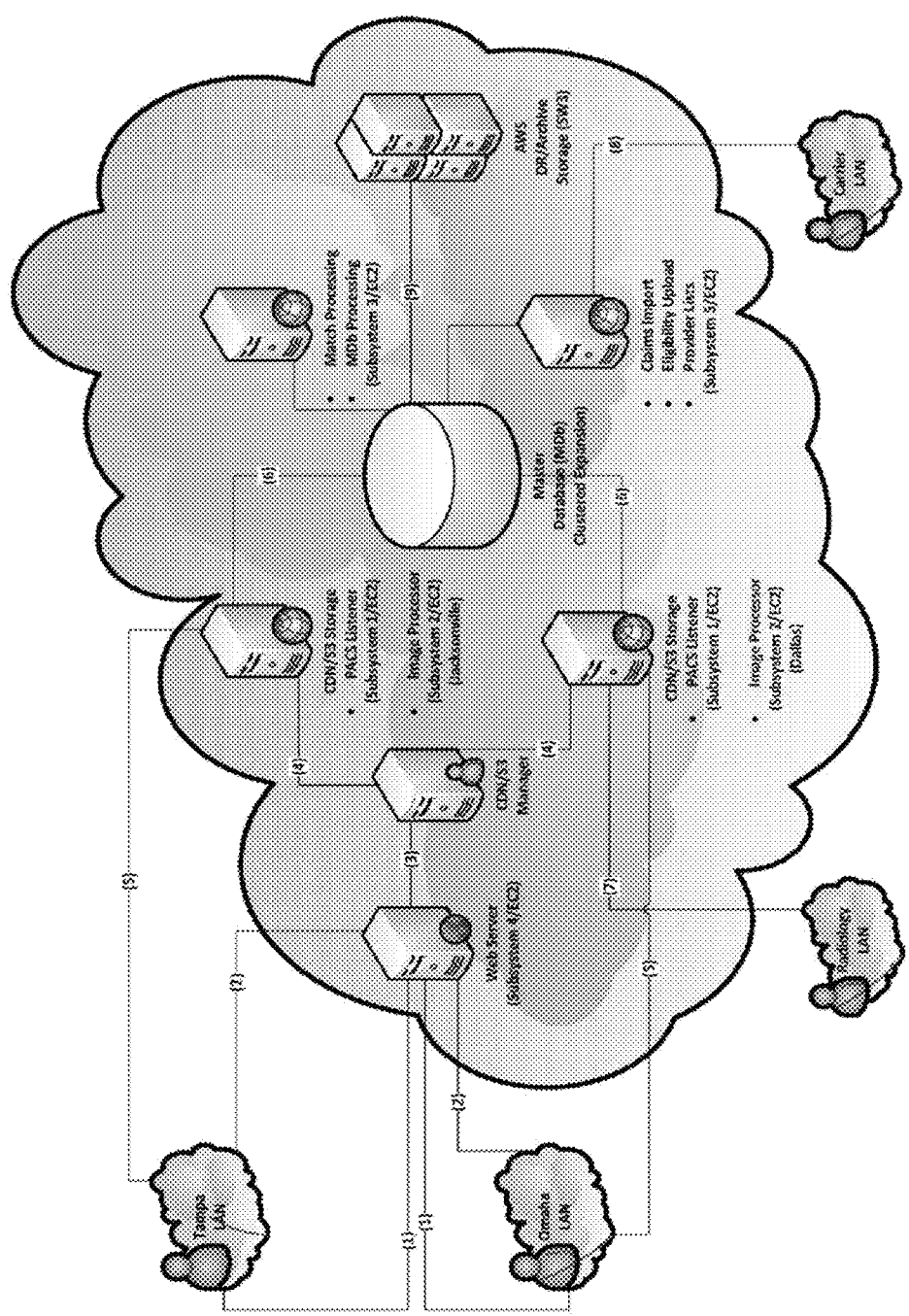
FIG. 49 is a high level schematic diagram illustrating the interrelationship between major components of the present system.

The non-limiting exemplary embodiment(s) will now be described more fully hereinafter with reference to the accompanying drawings, in which a preferred embodiment of the disclosure is shown. Such exemplary embodiment(s) may, however, be embodied in many different forms and should not be construed as limited to the embodiment set forth herein. Rather, these embodiment(s) are provided so that this application will be thorough and complete, and will fully convey the true scope of the disclosure to those skilled in the art.

The below disclosed subject matter is to be considered illustrative, and not restrictive, and any appended claim(s) are intended to cover all such modifications, enhancements, and other embodiment(s) which fall within the true scope of the non-limiting exemplary embodiment(s). Thus, to the maximum extent allowed by law, the scope of the non-limiting exemplary embodiment(s) is to be determined by the broadest permissible interpretation of the claim(s) and their equivalents, and shall not be restricted or limited by the foregoing detailed description.

References in the specification to "an exemplary embodiment", "an embodiment", "a preferred embodiment", "an alternative embodiment" and similar phrases mean that a particular feature, structure, or characteristic described in connection with the embodiment(s) is included in at least an embodiment of the disclosure. The appearances of the phrase "a non-limiting exemplary embodiment" in various places in the specification are not necessarily all meant to refer to the same embodiment.

The disclosure is a cloud-based radiology DICOM receipt, storage and management system interacting with payers (including insurance carriers, Radiology Benefit Management Companies, Disability Insurance Carriers, Automobile Insurance Carriers, Dental Carriers, etc.) in order reduce fraud and waste.

Referring to FIGS. 2-7 and 49, in a non-limiting exemplary embodiment, a client request arrives to a web interface at www.gensisvault.com, for example. The web interface returns the website/index pages. Next, the web interface redirects an object request to CDN manager. In response to the requests, the CDN manager forwards object request to nearest CDN/S3, wherein the nearest CDN/S3 delivers the selected object request. The CDN/S3 reads metadata and writes image records in the primary database (MDb). A radiology provider provides source objects to a PACS listener, then the carrier provides the source objects to a claims report. Finally, the MDb writes the source objects to an archive storage.

In a non-limiting exemplary embodiment, functions of the disclosure are performed a plurality of subsystems. For example, subsystem 1 is a picture archiving and communication system (PACS) listener. Subsystem 2 is an image processor that creates JPEG® images, reads metadata, creates image records in the MDb, and backs up files to Simple Storage Service (S3 storage). Subsystem 3 matches an MDb image to a patient, and an MDb claim. Subsystem 4 provides a web interface. Subsystem 5 imports claims, uploads eligibility requirements and provider lists.

In a non-limiting exemplary embodiment, subsystem 1 provides a Picture Archiving and Communication System (PACS) Listener wherein we use a PACS server, currently a package developed by LEADTOOLS®, to listen for DICOM images over TCP/IP. Once submitted to our system, we save the image to a specified directory, subsystem 2 (described hereinbelow) picks up the file and continues to process it through the system. This allows us to receive imaging files directly from digital imaging machines. Insurance carriers maintain relationship with radiology providers. Each provider that is a designated provider of the payer will go through an onboarding process with our company in order to complete submissions of DICOM studies related to that payer in an automated fashion utilizing a PACS listening application.

In a non-limiting exemplary embodiment, once a DICOM study has been submitted to our system, subsystem 2 "grabs" each image from the study (multiple images in each study) and processes that image into our long term storage and stores in the system database all of the metadata related to each image. Thus, subsystem 2 functions as a DICOM processor wherein it preferably creates .jpg images, reads metadata, creates image records in the Master Database (MDb), backs up files to AMAZON's S3 storage environment, etc.

Subsystem 2 may also process the file into the AMAZON S3 storage, for example. It also creates small and large thumbnails which are shown to the user inside the web portion of the software application. This processes the file and metadata stored on the image into the database so we can access the database rather than access the file from hard disk thereby saving a lot of disk I/O (input/output). In addition, subsystem 2 may create a study that will be later tied to a claim number.

In a non-limiting exemplary embodiment, subsystem 2 regularly picks up files received from the PACS listener, registers the file and its metadata into our system as an image study record, and backs up the original file to the AMAZON S3 bucket that is tied to a Content Delivery Network (CDN). CDNs allow for geographically localized delivery of files to reduce propagation delay during the file transfer. It also creates thumbnails of the DICOMS in varying sizes for quick: view in the web application.

In a non-limiting exemplary embodiment, subsystem 3 provides a match processing function in which it attempts to match the patient image with a patient record (previously provided by the payer) thus matching a member to an insurance policy, payer and provider. This may be performed by utilizing the metadata from each image including data items such as patient name, provider facility, machine name, machine type, model number, serial number, patient insurance ID, etc.

In a non-limiting exemplary embodiment, subsystem 3 matches the MDb image to a patient match process. For example, at regular intervals, the match processor matches image study records created in subsystem 2 with various non-image records from subsystem 5 (described hereinbelow). Unmatched records will set various flags for both payers and the imaging providers to see from the application in subsystem 4 (described hereinbelow), depending on what part of the record is lacking, or how long the record has been incomplete.

In a non-limiting exemplary embodiment, subsystem 3 may also match an insurance claim with a provider. If the image doesn't match, it is flagged with a status and is shown inside of the web application as error and is also flagged in reports that will be sent to insurance agencies on a daily occurrence.

In a non-limiting exemplary embodiment, subsystem 4 provides a user interface via a web browser. Thus, subsystem 4 acts as a user interface presented via a web application that interacts with the DICOM studies, primary database (MDb) and clients. The web application is used for human interaction with the records, reports, management, for administrators, providers, and payers. Thus, subsystem 4 provides a reporting system, process workflow, claim review, patient review, provider review, DICOM image review, etc. For example, a user may generate and run reports, overall management of the application for users, radiologist, insurance agencies managers, and administrators of the system.

In a non-limiting exemplary embodiment, subsystem 5 functions as a records input wherein it interacts in a back office fashion with payers by downloading and integrating at least three files (provider, eligibility and claims). These three files can be setup to import and reconcile at different intervals based on the needs of the payer (daily, weekly, monthly or custom). For example, at regular intervals, subsystem 5 imports the latest claims records, provider records, and eligibility records from payer companies. To accomplish this, we acquire data for our system from: a) image studies from digital imaging machines, b) claims made to payers by their clients, and c) patient eligibility records from the payers.

In a non-limiting exemplary embodiment, subsystem 5 further provides the following functions: imports claim/eligibility files in (CSV file format) from insurance agencies on a nightly basis. We developed a solution whereby payer companies can verify the authenticity of digital imaging claims received from their clients against the actual digital image the client produced. The primary goal of our disclosure is to reduce waste and eliminate fraud for payer companies originating from digital imaging. This solution includes multiple parts, a series of subsystems designed to import and match data, as well as a web application for our users to resolve issues found by our system and flagged on their data.

In a non-limiting exemplary embodiment, subsystem 5 provides the functions of: importing claims, uploading eligibility and displaying a provider list. As an example, a virtual cloud based application is provided for a centralized repository for diagnostic images wherein medical communities are integrated with insurance carriers. Subsystem 5 focuses on connecting all segments of the healthcare industry with the imaging repository thereby establishing accountability between the medical provider and the payer while adding the imaging component currently absent from the majority of EMR systems.

The present disclosure provides a method for facilitating a cloud-based radiology DICOM receipt, storage and management system. The method includes the steps of: providing a web-based portal; providing a centralized repository; and communicatively coupling the web-based portal with the centralized repository thereby enabling archival, retrieval and transferal of a medical diagnostic image between an insurance service provider and a medical service provider.

In a non-limiting exemplary embodiment, the method further includes the step of: reducing duplicate and inappropriate utilization of diagnostic medical diagnostic imaging services by providing, on the web-based portal, a first user interface enabling the medical service provider and the insurance service provider to simultaneously view the medical diagnostic image stored at the centralized repository.

In a non-limiting exemplary embodiment, the method further includes the step of: reducing medical claim fraud by providing, on the web-based portal, a second user interface enabling the medical service provider and the insurance service provider to cross-reference the medical diagnostic image with an associated medical claim form generated by the medical service provider.

In a non-limiting exemplary embodiment, the method further includes the steps of: validating a technical quality of the medical diagnostic image by providing, on the web-based portal, a third user interface enabling the medical service provider to flag the medical diagnostic images having poor technical quality; and automatically notifying the insurance service provider of the flagged medical diagnostic images.

In a non-limiting exemplary embodiment, the method further includes the step of: searching and identifying medical diagnostic modalities performed by the medical service provider by providing, on the web-based portal, a fourth user interface enabling the insurance service provider to route a patient to an approved one of the medical service providers that performs an authorized one of the medical diagnostic modalities required to diagnose the patient.

In a non-limiting exemplary embodiment, the method further includes the steps of: reducing preventable patient medical conditions and hospitalizations by providing, on the web-based portal, a fifth user interface enabling a first one of the medical service provider to identify if the medical diagnostic image shows an abnormal result; and notifying a second one of the medical service provider and the insurance service provider of the abnormal result.

In a non-limiting exemplary embodiment, the method further includes the step of: generating comprehensive data and analytics of the medical diagnostic image by providing, on the web-based portal, a sixth user interface enabling the insurance service provider to capture information regarding a patient, a medical modality, a medical procedure, a medical diagnostic facility as well as a medical diagnostic imaging machine operated by the medical service provider at the medical diagnostic facility.

In a non-limiting exemplary embodiment, the method further includes the step of: identifying a clinical appropriateness of an authorizing radiology imaging procedure by providing, on the web-based portal, a seventh user interface enabling the insurance service provider to search clinical radiology appropriateness criteria guidelines for a radiology imaging procedure to be performed by the medical service provider.

In a non-limiting exemplary embodiment, the method further includes the step of: channeling an independent imaging study of the medical diagnostic image generated by a first one of the medical service provider operating at a first location by providing, on the web-based portal, an eighth user interface enabling the insurance service provider to route the medical diagnostic image to a second one of the medical service provider operating at a second location remote from the first location.

In a non-limiting exemplary embodiment, the method further includes the step of: channeling a patient to one of the medical service provider having a preferred contracted rate by providing, on the web-based portal, a ninth user interface enabling the insurance service provider to upload and maintain the medical service provider contracted rates.

In a non-limiting exemplary embodiment, the method further includes the step of: facilitating epidemiology studies by providing, on the web-based portal, a tenth user interface enabling the insurance services provider to capture and query diagnostic results of the medical diagnostic images.

Searchable Database

As part of the process of the provider signup, the provider must complete a profile which provides full details of their operation to the payer and thus providing a data repository for the payer to search. An invitation email is sent from the system to the provider as part of the provider signup process. The provider must complete a validation/password step in the provider signup process to validate their base record. This data is exposed in the searchable interface for payers. The provider location and modality configuration screens are used heavily when providing search functionality to payers. A provider administration screen is provided so that each provider manager can manage their own provider profile. A Provider Search Function and Search Results is provided. Using few or several different types of data, users can search for patient records and retrieve results based on patient file.

An image work flow process is displayed from the visual interface. The first step is the Required Field Matcher. Based on the Member Eligibility data set available in the system, the system attempts to match the patient record automatically. If an automatic match cannot be made, a manual search and match function is available at this step in the process. The Provider Assignment and Clinical Notes screens of the Image/Study Workflow Process is displayed to allow the Provider requesting the Study to be assigned and the upload of the clinical notes/reads of the images/study.

Duplication of Imaging

A machine configuration setup document provides the ability for each provider to configure their machines to send one test image each with a key code on one of the user editable fields in order to full match each machine (as configured in the machines configuration process) to a unique code in the system. Each machine is clearly identified and each image from each provider is tracked for duplication. A Payer/Carrier Report Dashboard and Duplicates Denied report is provided along with a Payer/Carrier Potential Duplicates and Prevention Query Reports. The Payer/Carrier STAT Reads by Radiologist and Review Possible Claim Anomalies Report. STAT reads are often used to duplicate something that has already been done at another provider.

A Provider Search Function and Search Results screen allows searching functions. Using few or several different types of data, users can search for patient records and retrieve results based on patient file.

The Provider DICOM Image Viewer and QA Tagging Screen can be used to real time view the DICOM image from a patient record. The DICOM Quick View and DICOM Download Disposition screen allows for users to see a quick view of a large JPG file as opposed to downloading the entire DICOM image. The DICOM download screen requires users to assess why they are downloading an image.

Claim Fraud

The provider signup process is part of the onboarding program of the payer. As part of the process of the provider signup, the provider must complete a profile that tightly binds all studies/images to that provider as part of the image send process. This allows for automated tracking of the image throughout the system and provides for checks and balances for claim fraud. The provider location and modality configuration screens are part of the provider signup process. One of the matches to be provided in the claim fraud section is in the case of a provider billing for a modality or location that is not part of their profile.

A Payer/Carrier Quality Assurance Score Reports and ROI for Claim Anomaly Reports is made available along with the Payer/Carrier STAT Reads by Radiologist and Review Possible Claim Anomalies Report. A Payer/Carrier Review Actual Claim Anomalies and Provider Dashboard are provided to grant access to the Provider Search Function and Search Results. As noted above, using few or several different types of data, users can search for patient records and retrieve results based on patient file.

The first step in the image work flow process from the visual interface is the Required Field Matcher. Based on the Member Eligibility data set available in the system, the system attempts to match the patient record automatically. If an automatic match cannot be made, a manual search and match function is available at this step in the process.

A provider Assignment and Clinical Notes screens of the Image/Study Workflow Process. This part of the process allows the Provider requesting the Study to be assigned and the upload of the clinical notes/reads of the images/Study. A transcription and signing of the medical notes/records allows for the recording of the study notes and official sign off by the provider of the record.

Clinical Appropriateness

The Provider Search Function and Search Results and the Provider DICOM Image Viewer and QA Tagging Screen are used to perform this function.

Technical Quality of Image

As mentioned above, each image is matched to the provider as part of the signup process and thus can be traced back to each individual provider. The machine configuration setup document provides the ability for each provider to configure their machines to send one test image each with a key code on one of the user editable fields in order to full match each machine (as configured in the machines configuration process) to a unique code in the system. The Payer/Carrier Quality Assurance Score Reports and ROI for Claim Anomaly Reports and the Provider Search Function and Search Results, and the Provider DICOM Image Viewer and QA Tagging Screen are used to perform this function.

Channeling Imaging Studies

The Provider Assignment and Clinical Notes screens of the Image/Study Workflow Process allow the Provider requesting the Study to be assigned and the upload of the clinical notes/reads of the images/Study. A display of the transcription and signing of the medical notes/records provided. This allows for the recording of the study notes and official sign off by the provider of the record.

Inappropriate Admissions

The Payer/Carrier Hospital Admissions Reduction and Modality Reports By Radiologist provide data on inappropriate admissions. The Payer/Carrier Potential Duplicates and Prevention Query Reports are used to perform this function.

Contract Rates

The Payer/Carrier STAT Reads by Radiologist and Review Possible Claim Anomalies Report performs this function. STAT reads also affect rates.

Data and Analytics

Provider location and modality configuration screens are part of the provider signup process and collect data that is used to build the data repository necessary for analytics. The machine configuration setup document that provides the ability for each provider to configure their machines to send one test image each with a key code on one of the user editable fields in order to full match each machine (as configured in the machines configuration process) to a unique code in the system. The provider administration screen allows each provider manager to manage their own provider profile. The Payer/Carrier Report Dashboard and Duplicates Denied report, the Payer/Carrier Hospital Admissions Reduction and Modality Reports by Radiologist, the Payer/Carrier Potential Duplicates and Prevention Query Reports, the Payer/Carrier Provider Profile Report and Provider Setup Completion Report, the Payer/Carrier Quality Assurance Score Reports and ROI for Claim Anomaly Reports, the Payer/Carrier STAT Reads by Radiologist and Review Possible Claim Anomalies Report, the Payer/Carrier Review Actual Claim Anomalies and Provider Dashboard, and the Provider Search Function and Search Results are used to perform this function.

The DICOM Quick View and DICOM Download Disposition download screen requires users to assess why they are downloading an image. The Provider Assignment and Clinical Notes screens of the Image/Study Workflow Process allow the Provider requesting the Study to be assigned and the upload of the clinical notes/reads of the images/Study displays the transcription and signing of the medical notes/records. This allows for recording of the study notes and official sign off by the provider of the record.

Provider Signup Process

A provider signup process is made part of the onboarding program of the payer. An invitation email is sent from the system to the provider as part of the provider signup process. The validation/password step is part of the provider signup process that the provider must complete to validate their base record. Provider location and modality configuration screens are displayed and the provider must accept the provider user assignment and Terms of Use acceptance screens. A provider Business Associate Agreement acceptance and confirmation email is sent with next steps for the provider. The provider manager must accept the Business Associate Agreement for the provider for the entire provider to participate in the process. The machine configuration setup document provides the ability for each provider to configure their machines to send one test image each with a key code on one of the user editable fields in order to full match each machine (as configured in the machines configuration process) to a unique code in the system. The administrator is able to Manage Failed Provider authorization attempts and to Manage Users. Managing failed authorization attempts is a response to the provider signup process when providers authorize machines to utilize the system.

Payer/Carrier Functions

Such functions are provided by the Payer/Carrier Dashboard for each Payer in the system, the Payer/Carrier Report Dashboard and Duplicates Denied report, the Payer/Carrier Hospital Admissions Reduction and Modality Reports by Radiologist, the Payer/Carrier Potential Duplicates and Prevention Query Reports, the Payer/Carrier Provider Profile Report and Provider Setup Completion Report, the Payer/Carrier Quality Assurance Score Reports and ROI for Claim Anomaly Reports, the Payer/Carrier STAT Reads by Radiologist and Review Possible Claim Anomalies Report, and the Payer/Carrier Review Actual Claim Anomalies and Provider Dashboard.

Provider Functions

Such functions are provided by the Payer/Carrier Review Actual Claim Anomalies and Provider Dashboard, the Provider Report Dashboard and the Modality Reports by Radiologist, the Provider Search Function and Search Results, the Provider DICOM Image Viewer and QA Tagging Screen, and the DICOM Quick View and DICOM Download Disposition screen. The DICOM Quick View allows for users to see a quick view of a large JPG file as opposed to downloading the entire DICOM image. The DICOM download screen requires users to assess why they are downloading an image.

Image/Study Workflow Processing

The first step in the image work flow process from the visual interface is the Required Field Matcher. Based on the Member Eligibility data set available in the system, the system attempts to match the patient record automatically. If an automatic match cannot be made, a manual search and match function is available at this step in the process. The Provider Assignment and Clinical Notes screens of the Image/Study Workflow Process allow the Provider requesting the Study to be assigned and the upload of the clinical notes/reads of the images/Study. The transcription and signing of the medical notes/records allows for recording of the study notes and official sign off by the provider of the record. The claim match screen for an image/study displays the results of a claim match for that study in the system. The Administrator Dashboard is the default dashboard for administrative purposes.

Administrator Functions

A display of the claim match screen for an image/study as well as the Administrator Dashboard is provided. The claim match screen displays the results of a claim match for that study in the system. A display of the Administrator Search functionality and search results screen is also provided. The Administrative Report Dashboard as well as the Provider Setup Completion Report display statuses for providers in their configuration process.

A report for Subsystem 1 and the report for Subsystem 2 are provided. The Subsystem 1 report displays what files have been received. The Subsystem 2 report tracks the processing of those files through Subsystem 2.

Also, a technical support page for users is provided along with a page to manage each roles links/functions inside the application. The administrator has the ability to manage agreement types and to manage carrier/payer links/functions. The agreement types must be presented to appropriate users upon first signing in to the application. The Manage Carriers/Payers and Manage Locations functionality allows the administrator can add/edit/delete which carriers/payers are authorized to utilize the system and to manage which locations are available to those carriers/payers. The Manage Machines and Manage Providers functionality provides the administrators the ability to add/edit/delete machines as well as to manage the providers. The Manage Providers to Carriers as well as the Manage QA Tags functionality allows administrators the ability to tie providers to one to many payers/carriers. The Manage QA functionality allows administrators the ability to add QA tags to the system that are then displayed to the providers. A screen displays the functionality for the administrator to Mange Reports and Manage Roles for permissions. Another screen displays the functionality for the administrator to manage Roles for Reports and to Manage Roles for Users. The ability for the administrator to Manage Failed Provider authorization attempts and to Manage Users is also provided. Managing failed authorization attempts is a response to the provider signup process when providers authorize machines to utilize the system. Another screen provides the ability for the administrator to Manage Users to Carriers/Payers and Manage Users to Providers. This allows users to be tied to individual Payers and/or Providers.

In a non-limiting exemplary embodiment, the disclosure is a software application (computer program product) designed to provide the following health care and health information benefits: 1. Reduce duplication of radiology images and related services. 2. Reduce insurance claim fraud for radiology services. 3. Promote quality assurance (QA) and reporting of radiology image quality. 4. Provide a searchable database. 5. Provide data analytics. 6. Decrease hospital admissions. 7. Provide protocol and role-based approvals. 8. Promote teleradiology services.

In a non-limiting exemplary embodiment, present disclosure provides a group of software applications (computer program product) called 'subsystems' to handle various tasks. The image study records are received by a PACS server, made for sending and receiving files over TCP/IP in the DICOM file format used by digital imaging devices in the healthcare industry. The additional non-image records are imported into the system via more conventional data feed mechanisms such as, but not limited to, JSON, XML. As they enter our system, the studies are converted to our data structure for handling these unified records.

In a non-limiting exemplary embodiment, the benefits of the software application (computer program product) include, inter alia, the functions of:

Significantly Reduces Duplication and Inappropriate Utilization of Diagnostic Imaging Reduces Claim Fraud and Abuse Assures Technical Quality of Images Lacking Quality Assurance Validation Ability to Generate Comprehensive Data and Analytics for Imaging and Radiology Appropriately Utilizes Diagnostic Imaging to Address Preventable Conditions and Hospitalizations Instant Access to Identify Specific Modalities Performed by Diagnostic Providers Implement American College of Radiology (ACR) medical utilization guidelines Permits Carrier to view physician report w/image-currently not available Tracks Historical Progression of Patient Diagnosis and Treatment Reduces Unproductive & Costly Medical Specialist Consultations Reduces Unnecessary Radiation Exposure to Patient- Reduces Malpractice law suits Access to Archived Diagnostic Studies Reduces Defensive Medicine Performed by Physicians, Reducing Over Utilization Decreases Physician Owned Diagnostic Center Self Referrals Reduces Additional Patient Co-pays Provides central repository for image storage Provides data backup & recovery Provides integrated DICOM image viewer The software application (computer program product) is an Internet accessible, cloud-based product which stands on AMAZON's Web Services (AWS) infrastructure. The application infrastructure preferably contains 5 sub-systems but may contain less or more sub-systems in alternate embodiment(s).

In a non-limiting exemplary embodiment, the computer software (computer program product) has the ability to tie a radiology image to a claim and eligibility files for insurance agencies. To accomplish this task we had to split the actions of the system into multiple subsystems, a description of each function is listed below. This technology will greatly help reduce cost for insurance agencies by lowering re-reads and fraud prevention. But the impact will also help with individual health and well-being by creating a ownership process for reading/dictating the radiology image.

In a non-limiting exemplary embodiment, a goal of our application, loaded with the appropriate data sources, is to make a three-fold match between new image studies received by the PACS listener, patient eligibility records, and payer claims. We automatically validate these claims through our custom auto-matching subsystem. The records, in all states of matching, are available to the clients via our web application.

An incomplete image or claim record, (one that did not achieve a three-fold match), can be manually resolved by the imaging provider or payer via this application. Records that are not resolved promptly by the imaging provider are the most likely candidates for fraudulent claims; such information is also made available to the payers via various reports in the web application. We also provide extra advantages for the imaging provider, allowing them to request a digital over read or a second opinion on the reading of an image, to mark the image record as abnormal, and access our digital backup of the original digital image record we received via the web application.

In a non-limiting exemplary embodiment, the an important piece to our solution is scalability. There are two aspects to this problem. The first is the raw input our system will have to face. A DICOM file can be quite large, and we will need to be able to handle large volumes of them being sent to our system simultaneously. The second aspect is the rate at which we need to be able to onboard new patients; to be able to easily expand the volume that our system can handle this load.

Our solution to these problems is simpler to explain in reverse. Many years ago, expanding the maximum capacity of servers was very expensive. If it took 100 servers to meet your maximum load in during daytime peak hours, you necessarily had 100 servers at night as well, each machine you bought to expand your maximum server load was a physical machine in your possession. Leveraging the advent of cloud infrastructure, specifically AMAZON Web Services (AWS) in our prototype, our answer was elastic architecture. 'Machines' that house subsystems are in fact 'virtual machines' on AMAZON and similar cloud-based services. By creating virtual machine archetypes, templates for servers, developed to work in an elastic array of these mirrored virtual machines, we can spin new machines up, or remove them, at will. We can plan for doubling the supported work load by increasing the number of virtual machines in our elastic array without having to worry about the inhibiting temporal and physical overhead of actually purchasing, configuring, and maintaining the hardware of physical servers.

We developed our elastic arrays of virtual machine templates with the ability to shrink on the fly, not only to grow. By continuously monitoring and compensating for the current demand on system resource usage, we can grow to meet peak demands, and shrink during hours with lesser traffic to minimize cost. We have designed this set of elastic arrays by virtual machine template type so that we can cater our scalability to the types of tasks these virtual servers accomplish.

In a non-limiting exemplary embodiment, subsystems 1 and 2 are on the same virtual machine template, so that we can scale from 1-n servers as needed, each with a copy of Subsystems 1 and 2, designed to work in such a parallel fashion. In like fashion, subsystems 3 through 5 each have their own virtual machine templates. The database clusters sit on another template type of these virtual machine nodes. This approach is what allows us to independently scale our resources for receiving and processing image records (SS1+ 2), importing non-image records from payer companies (SS5), automatically match the various data sources into a unified record (SS3), as well as to scale the web application our clients use (SS4).

Advantageously, these are the base processes by which we source our data, create a unified image record, identify possibly fraudulent records, allow users to interface with the data, and are able to do it all in a scalable fashion suited for rapid deployment.

Conventional medical image storage management companies currently provide limited solutions, such as www-.seemyradiology.com, available for radiology providers to have secure off-site backups of patient images, with an online DICOM viewer and other radiologist-focused tools. Some of these companies also make the images available for viewing by the patient. These solutions are catered in particular to healthcare providers and/or their patients. Thus, www.seemyradiology.com merely offers off-site backups and image exchange as the focus of their solution.

Our solution offers this functional capability as well, but on its way to a different primary focus as an application. In particular, our solution differs from such an aforementioned attempt because, inter alia, our primary goal is to reduce waste and fraud for payer companies that make use of digital imaging technologies. We keep image backups as evidence of validated, or possibly fraudulent, records as part of that goal. Simple redistributing the backups to our users, healthcare providers and the payer companies, gives us an overlap in a functional capability sense.

In one embodiment, the disclosure is directed toward one or more computer systems capable of carrying out the functionality described herein. An example of a computer system (device) 100 is shown in FIG. 1.

FIG. 1 sets forth illustrative computing device 100 that may be used to implement any aspect of the functions described above. For example, computing device 100 may be used to implement any aspect of the present disclosure.

In all cases, computing device 100 represents one or more physical and tangible processing mechanisms.

Computing device 100 includes a communications infrastructure 106 that transmits/receive information from processor 104, main memory 108, display interface 102, secondary memory 110, and communications interface 124, for example. Display interface 102 provides images on a display 135. The secondary memory 110 may include a hard disk drive 112, removable storage drive 114 and/or interface 125. Such components receive information from removable storage units 118, 122. The communications interface 124 transmits information via a communications conduit 128. Such information is transmitted/received from an external source via a communications path 126.

Computing device 100 may also include volatile and non-volatile memory, such as RAM and ROM, as well as one or more processors 104 (e.g., one or more CPUs, and/or one or more GPUs, etc.). Computing device 100 may also include various media devices, such as a hard disk module, an optical disk module, and so forth. The computing device 100 can perform various operations identified above when the processor 104 executes instructions that are maintained by memory (e.g., RAM, ROM or elsewhere).

More generally, instructions and other information may be stored on any computer readable medium including, but not limited to, static memory storage devices, magnetic storage devices, optical storage devices, and so on. The term "computer readable medium" also encompasses plural storage devices. In all cases, computer readable medium represents some form of physical and tangible entity. By way of example, and not limitation, computer readable medium may comprise computer storage media and communications media.

Communication media typically embody computer readable instructions, data structures, program modules, or other data in a modulated data signal, such as carrier wave or other transport mechanism. Communication media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media. Combinations of any of the above are also included within the scope of computer readable media.

Computing device 100 also includes an input/output module for receiving various inputs (via input modules), and for providing various outputs (via one or more output modules). One particular output mechanism may include a presentation module and an associated GUI. Computing device 100 may also include one or more network interfaces for exchanging data with other devices via one or more communication conduits. One or more communication buses communicatively couple the above-described components together.

Communication conduit(s) 128 may be implemented in any manner (e.g., by a local area network, a wide area network (e.g., the Internet), etc., or any combination thereof). Communication conduit(s) can include any combination of hardwired links, wireless links, routers, gateway functionality, name servers, etc., governed by any protocol or combination of protocols.

Alternatively, or in addition, any of the functions described herein can be performed, at least in part, by one or more hardware logic components. For example, without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

The terms "module" and "component" as used herein generally represent software, firmware, hardware, or combinations thereof. In the case of a software implementation, the module or component represents program code that performs specified tasks when executed on a processor. The program code can be stored in one or more computer readable memory devices, as described with reference to FIG. 3 The features of the present disclosure described herein are platform-independent, meaning that the techniques can be implemented on a variety of commercial computing platforms having a variety of processors (e.g., desktop, laptop, notebook, tablet computer, personal digital assistant (PDA), mobile telephone, smart telephone, gaming console, and the like).

Each of the above methods may be executed using one or more processors on one or more computer devices 100. Embodiments may include various forms of distributed computing, client/server computing, and cloud based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, by a computer system, and so on. Any and all of which may be generally referred to herein as a "circuit," "module," or "system."

A programmable apparatus which executes any of the above mentioned computer program products or computer implemented methods may include one or more processors, microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computing device 100 may include a computer program product from a computer-readable storage media and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present disclosure are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random access memory (RAM), a read-only memory (ROM), an erasable programmable read-only memory (EPROM), Flash, MRAM, FeRAM, phase change memory, an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

There has thus been outlined, rather broadly, the more important features of the disclosure in order that the detailed description thereof that follows may be better understood, and in order that the present contribution to the art may be better appreciated.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the disclosure of the application, nor is it intended to be limiting as to the scope of the disclosure in any way.

What is claimed as new and what is desired to secure by Letters Patent of the United States is:

1. A method for providing a cloud-based radiology DICOM receipt, storage and management system, said method comprising the steps of:

providing a web-based portal;

providing a centralized repository;

communicatively coupling said web-based portal with said centralized repository thereby archiving, retrieving, and transferring a medical diagnostic image between an insurance service provider and a medical service provider; and providing a host server remotely located from said web-based portal, said host server being communicatively coupled to said web-based portal and said centralized repository, said host server including a processor and a memory in communication therewith, said memory including software instructions that automatically execute an algorithm including the steps of:

upon receiving a first user input at said web-based portal, automatically and electronically reducing duplicate and inappropriate utilization of diagnostic medical diagnostic imaging services by providing, on said web-based portal, a first user interface simultaneously displaying, to the medical service provider and the insurance service provider, the medical diagnostic image stored at said centralized repository;

upon receiving a second user input at said web-based portal, automatically and electronically reducing medical claim fraud by providing, on said web-based portal, a second user interface cross-referencing and displaying, to the medical service provider and the insurance service provider, the medical diagnostic image with an associated medical claim form generated by the medical service provider;

wherein said step of automatically and electronically reducing medical claim fraud comprises the sub-steps of automatically and electronically matching the medical diagnostic image with at least one identifying characteristic of a patient record, automatically and electronically matching a patient to the medical service provider and an insurance policy of the insurance service provider, wherein said at least one patient identifying characteristic is selected from medical diagnostic image metadata including at least one of: a patient name, a medical service provider facility, a machine name of the medical service provider, a machine type of the medical service provider, a model number of the machine type, a serial number of the machine type, and a patient insurance ID, automatically and electronically, at regular intervals, matching patient diagnostic image records with various patient non-image records, automatically and electronically, flagging unmatched patient diagnostic image records for both the insurance service provider and the medical service provider, and automatically and electronically, learning one of: which part of the patient diagnostic image records is lacking and how long the patient diagnostic image records have been incomplete;

wherein said algorithm further comprises the chronological steps of:

automatically and electronically validating a technical quality of the medical diagnostic image by providing, on said web-based portal, a third user interface flagging the medical service provider the medical diagnostic images having poor technical quality; and automatically and electronically notifying the insurance service provider of the flagged medical diagnostic images;

wherein said step of automatically and electronically validating the technical quality of the medical diagnostic image comprises the sub-step of matching the medical diagnostic image to the medical service provider as part of a signup process by configuring a machine of the medical service provider by receiving from each medical service provider a machine configuration setup document, sending a test image with a key code on one of a plurality of user editable fields to match the medical service provider machine to a unique code, and tracing back the medical diagnostic image to the associated individual medical service provider.

2. The method of claim 1, wherein said algorithm further comprises the step of:

automatically and electronically searching and identifying medical diagnostic modalities performed by the medical service provider by providing, on said web-based portal, a fourth user interface routing a patient, from the insurance service provider, to an approved one of the medical service providers that performs an authorized one of said medical diagnostic modalities required to diagnose the patient;

wherein said step of automatically and electronically searching and identifying medical diagnostic modalities performed by the medical service provider comprises the sub-steps of during a medical service provider signup, receiving from the medical service provider a profile including medical service provider operation details, creating a data repository for the insurance service provider to search, and exposing, to the insurance service provider, a searchable interface identifying a location and a modality configuration of the medical service provider profile.

3. The method of claim 1, wherein said algorithm further comprises the chronological steps of:

automatically and electronically reducing preventable patient medical conditions and hospitalizations by providing, on said web-based portal, a fifth user interface identifying to, a first one of the medical service provider, if the medical diagnostic image shows an abnormal result; and notifying a second one of the medical service provider and the insurance service provider of the abnormal result;

wherein the step of automatically and electronically reducing preventable patient medical conditions and hospitalizations comprises the sub-steps of identifying, to a medical service provider specialist, if the patient diagnostic image of the medical service provider is abnormal, and upon learning, from the medical service provider specialist, that said patient diagnostic image is abnormal, notifying a referring medical service provider and the insurance service provider that the patient needs follow up medical care.

4. The method of claim 1, wherein said algorithm further comprises the step of:

automatically and electronically generating comprehensive data and analytics of the medical diagnostic image by providing, on said web-based portal, a sixth user interface capturing, for the insurance service provider, information regarding a patient, a medical modality, a medical procedure, a medical diagnostic facility as well as a medical diagnostic imaging machine operated by the medical service provider at the medical diagnostic facility.

5. The method of claim 1, wherein said algorithm further comprises the step of:

automatically and electronically identifying a clinical appropriateness of an authorizing radiology imaging procedure by providing, on said web-based portal, a seventh user interface searching, for the insurance service provider, clinical radiology appropriateness criteria guidelines for a radiology imaging procedure to be performed by the medical service provider.

6. The method of claim 1, wherein said algorithm further comprises the step of:

automatically and electronically channeling an independent imaging study of the medical diagnostic image generated by a first one of the medical service provider operating at a first location by providing, on said web-based portal, an eighth user interface routing, from the insurance service provider, the medical diagnostic image to a second one of the medical service provider operating at a second location remote from said first location.

7. The method of claim 1, wherein said algorithm further comprises the step of:

automatically and electronically channeling a patient to one of the medical service provider having a preferred contracted rate by providing, on said web-based portal, a ninth user interface uploading and maintaining from, the insurance service provider, the medical service provider contracted rates.

8. The method of claim 1, wherein said algorithm further comprises the step of:

automatically and electronically facilitating epidemiology studies by providing, on said web-based portal, a tenth user interface capturing and querying for, the insurance services provider, diagnostic results of the medical diagnostic images.

* * * * *